US012673139B2

(12) United States Patent
Kimicata et al.

(10) Patent No.: US 12,673,139 B2
(45) Date of Patent: Jul. 7, 2026

(54) 3D PRINTED UV CROSSLINKING MASKS

(71) Applicant: University of Maryland, College Park, College Park, MD (US)

(72) Inventors: Megan Kimicata, New Market, MD (US); John Patrick Fisher, Kensington, MD (US)

(73) Assignee: University of Maryland, College Park, College Park, MD (US)

( * ) Notice: Subject to any disclaimer, the term of this patent is extended or adjusted under 35 U.S.C. 154(b) by 795 days.

(21) Appl. No.: 17/930,469

(22) Filed: Sep. 8, 2022

(65) Prior Publication Data

US 2023/0082358 A1 Mar. 16, 2023

Related U.S. Application Data

(60) Provisional application No. 63/261,012, filed on Sep. 8, 2021.

(51) Int. Cl.
| | |
|---|---|
| *A61L 27/54* | (2006.01) |
| *A61L 27/36* | (2006.01) |
| *A61L 27/50* | (2006.01) |
| *A61L 33/00* | (2006.01) |
| *A61L 33/12* | (2006.01) |
| *B33Y 80/00* | (2015.01) |

(52) U.S. Cl.
CPC ........... *A61L 27/54* (2013.01); *A61L 27/3625* (2013.01); *A61L 27/507* (2013.01); *A61L 33/0011* (2013.01); *A61L 33/124* (2013.01); *B33Y 80/00* (2014.12)

(58) Field of Classification Search
None
See application file for complete search history.

(56) References Cited

U.S. PATENT DOCUMENTS

| | | | | | |
|---|---|---|---|---|---|
| 6,335,029 | B1 * | 1/2002 | Kamath | ................... | B05D 1/60 |
| | | | | | 424/487 |
| 6,379,382 | B1 * | 4/2002 | Yang | ....................... | A61L 31/12 |
| | | | | | 623/1.42 |
| 7,662,409 | B2 | 2/2010 | Masters | | |
| 9,795,471 | B2 | 10/2017 | Bracaglia et al. | | |
| 2010/0035838 | A1 | 2/2010 | Heber et al. | | |

FOREIGN PATENT DOCUMENTS

| | | | | | |
|---|---|---|---|---|---|
| CN | 103721293 | A | * | 4/2014 | |
| WO | WO-2019028494 | A1 | * | 2/2019 | ............... A61F 2/30 |

OTHER PUBLICATIONS

Yue et al. "Synthesis, properties, and biomedical applications of gelatin methacryloyl (GelMA) hydrogels", Biomaterials 73 (2015) pp. 254-271. (Year: 2015).*

Machine translation of CN 103721293 A. (Year: 2014).*
Kimicata et al. "Assessment of decellularized pericardial extracellular matrix and poly(propylene fumarate) biohybrid for small-diameter vascular graft applications", Acta Biomater. Jul. 1, 2020;110:68-81. (Year: 2020).*
Ling et al., "Effect of heparin on the biological properties and molecular signature of human mesenchymal stem cells", Gene, vol. 576, pp. 292-303, 2016.
Lip et al., "von Willebrand factor: a marker of endothelial dysfunction in vascular disorders?", Cardiovascular Research, vol. 34, pp. 255-265, 1997.
Löf et al., "A biophysical view on von Willebrand factor activation", J. Cell Physiol., vol. 233, pp. 799-810, 2018.
Luong-Van et al., "Controlled release of heparin from poly(e-caprolactone) electrospun fibers", Biomaterials, vol. 27, pp. 2042-2050, 2006.
Lupu et al., "Cellular Effects of Heparin on the Production and Release of Tissue Factor Pathway Inhibitor in Human Endothelial Cells in Culture", Arterioscler Thromb Vasc Biol., pp. 2251-2262, Sep. 1999.
Marcum et al., "Anticoagulantly Active Heparin-like Molecules from Vascular Tissue", Biochemistry, vol. 23, pp. 1730-1737, 1984.
Maroney et al., "Expression of tissue factor pathway inhibitor by endothelial cells and platelets", Transfusion and Apheresis Science, vol. 38, pp. 9-14, 2008.
Martinez-Salas et al., "Effect of unfractionated heparin and a low molecular weight heparin (enoxaparin) on coagulant activity of cultured human endothelial cells", Haematologica, vol. 88, pp. 694-699, Jun. 2003.
Matsagas et al., "Carotid Endarterectomy with Bovine Pericardium Patch Angioplasty: Mid-Term Results", CEA with BPPA, vol. 20, No. 5, pp. 614-619, 2006.
Mckavanagh et al., "Management and Prevention of Saphenous Vein Graft Failure: A Review", Cardiol Ther., vol. 6, pp. 203-233, 2017.
Mi et al., "Promoting endothelial cell affinity and antithrombogenicity of polytetrafluoroethylene (PTFE) by mussel-inspired modification and RGD/heparin grafting", Journal of Materials Chemistry B, vol. 6, pp. 3475-3485, 2018.

(Continued)

*Primary Examiner* — Carlos A Azpuru
*Assistant Examiner* — Casey S Hagopian
(74) *Attorney, Agent, or Firm* — McKee, Voorhees & Sease, PLC

(57) ABSTRACT

Current approaches in small diameter vascular grafts for coronary artery bypass surgeries fail to address physiological variations along the graft that contribute to thrombus formation and ultimately graft failure. An interlayer drug delivery system can sustain delivery of heparin through the graft with a high degree of temporal and spatial control. A heparin-loaded gelatin methacrylate interlayer sits between a biohybrid composed of decellularized bovine pericardium and poly(propylene fumarate) and UV crosslinking is controlled via 3D printed shadow masks. The masks enable control of the resultant gelMA crosslinking and properties by modulating the incident light intensity on the graft. High doses of heparin have detrimental effects on endothelial cell function. When exposed to heparin in a slower, more sustained manner consistent with the masks, endothelial cells behave similarly to untreated cells. Slower release profiles cause significantly more release of tissue factor pathway inhibitor, an anticoagulant, than a faster release profile.

13 Claims, 8 Drawing Sheets

(56)　　　　　　　References Cited

OTHER PUBLICATIONS

Peng et al., "A Novel Ovine ex vivo Arteriovenous Shunt Model to Test Vascular Implantability", Cells Tissues Organs, vol. 195, pp. 108-121, Oct. 14, 2011.

Pennel et al., "Transmural capillary ingrowth is essential for confluent vascular graft healing", Acta Biomaterialia, vol. 65, pp. 237-247, 2018.

Pepelanova et al., "Gelatin-Methacryloyl (GelMA) Hydrogels with Defined Degree of Functionalization as a Versatile Toolkit for 3D Cell Culture and Extrusion Bioprinting", Bioengineering, vol. 5, 15 pages, 2018.

Pixley et al., "Effect of Heparin on the Inactivation Rate of Human Activated Factor XII by Antithrombin III", Blood, vol. 66, pp. 198-203, 1985.

Poletti et al., "Structural Aspects of Heparin Responsible for Interactions With von Willebrand Factor", Arteriosclerosis, Thrombosis, and Vascular Biology, vol. 17, Issue 5, pp. 925-931, May 1997.

Qasim et al., "The Effect of Cross-linking Efficiency of Drug-Loaded Novel Freeze Gelated Chitosan Templates for Periodontal Tissue Regeneration", AAPS PharmSciTech, vol. 21, 9 pages, 2020.

Qiu et al., "End-point immobilization of heparin on plasma-treated surface of electrospun polycarbonate-urethane vascular graft", Acta Biomaterialia, vol. 51, pp. 138-147, 2017.

Quint et al., "Decellularized tissue-engineered blood vessel as an arterial conduit", PNAS, vol. 108, No. 22, pp. 9214-9219, May 31, 2011.

Ranjan et al., "Human Blood Vessel-Derived Endothelial Progenitors for Endothelialization of Small Diameter Vascular Prosthesis", PLoS One, vol. 4, Issue 11, 11 pages, Nov. 2009.

Rodriguez de Anda et al., "Effects of solvent used for fabrication on drug loading and release kinetics of electrosprayed temozolomide-loaded PLGA microparticles for the treatment of glioblastoma", Journal of Biomedical Materials Research Part B: Applied Biomaterials, 8 pages, published online Mar. 2019.

Rosenbaum et al., "Modulation of Endothelial Cells Growth Induced By Heparin", Cell Biology International Reports, vol. 10, No. 6, pp. 437-446, Jun. 1986.

Rumbaut et al., "Platelet-Vessel Wall Interactions in Hemostasis and Thrombosis", Morgan & Claypool Life Sciences Publishers, 74 pages, copyright 2010.

Sánchez et al., "Endothelialization mechanisms in vascular grafts", 10.1002/term.2747, 56 pages.

Schneider et al., "Acellular vascular matrix grafts from human placenta chorion: Impact of ECM preservation on graft characteristics, protein composition and in vivo performance", Biomaterials, vol. 177, pp. 14-26, 2018.

Schuurman et al., "Gelatin-Methacrylamide Hydrogels as Potential Biomaterials for Fabrication of Tissue-Engineered Cartilage Constructs", Macromolecular Bioscience, vol. 13, pp. 551-561, 2013.

Seeger et al., "Heparin Disrupts the CXCR4/SDF-1 Axis and Impairs the Functional Capacity of Bone Marrow-Derived Mononuclear Cells Used for Cardiovascular Repair", Circulation Research, pp. 854-862, Sep. 12, 2012.

Shi et al., "Proof of fallout endothelialization of impervious Dacron grafts in the aorta inferior vena cava of the dog", Journal of Vascular Surgery, vol. 20, No. 4, pp. 546-557.

Spadaccio et al., "Drug releasing systems in cardiovascular tissue engineering", J. Cell. Mol. Med. Vol 13, No. 3, pp. 422-439, 2009.

Strobel et al., "Targeted Delivery of Bioactive Molecules for Vascular Intervention and Tissue Engineering", vol. 9, Article 1329, 23 pages, Nov. 2018.

Tanaka et al., "Heparin anticoagulation in patients undergoing off-pump and on-pump coronary bypass surgery", vol. 21, pp. 297-303, 2007.

Tannenbaum et al., "Heparin Enhances Endothelial Cell von Willebrand Factor Content by Growth Factor Dependent Mechanisms", Thrombosis and Haemostasis, vol. 71(3), pp. 770-776, 1994.

Toursarkissian et al., "Thrombogenicity of small-diameter prosthetic grafts: Relative contributions of graft-associated thrombin and factor Xa", Journal of Vascular Surgery, vol. 25, No. 4, pp. 730-735, Apr. 1997.

Van Belleghem et al., "Hybrid 3D Printing of Synthetic and Cell-Laden Bioinks for Shape Retaining Soft Tissue Grafts", Adv. Funct. Mater., 10 pages, 2019.

Vigata et al., "Gelatin Methacryloyl Hydrogels Control the Localized Delivery of Albumin-Bound Paclitaxel", Polymers, vol. 12, 20 pages, 2020.

Vyslouzil et al., "Long-term controlled release of PLGA microparticles containing antidepressant mirtazapine", Pharm Dev Technol, 8 pages, 2014.

Wang et al., "Thrombotic Regulation From the Endothelial Cell Perspectives", Arterioscler Thromb. Vasc. Biol., 6 pages, Jun. 2018.

Watson, Steve P., "Platelet Activation by Extracellular Matrix Proteins in Haemostasis and Thrombosis", Current Pharmaceutical Design, vol. 15, pp. 1358-1372, 2009.

Yang et al., "The effect of heparin on osteoblast differentiation and activity in primary cultures of bovine aortic smooth muscle cells", Atherosclerosis, vol. 179, pp. 79-86, 2005.

Yang et al., "Mussel-Inspired One-Step Adherent Coating Rich in Amine Groups for Covalent Immobilization of Heparin: Hemocompatibility, Growth Behaviors of Vascular Cells, and Tissue Response", ACS Applied Materials & Interfaces, vol. 6, pp. 14608-14620, 2014.

Xu et al., "Heparin: an intervenor in cell communication", J. Cell. Mol. Med., vol. 14, No. 1-2, pp. 175-180, 2010.

Adams et al., "Tissue Factor Pathway Inhibitor Antigen and Activity in 96 Patients Receiving Heparin for Cardiopulmonary Bypass", Journal of Cardiothoracic and Vascular Anesthesia, vol. 16, No. 1, pp. 59-63, Feb. 2002.

Aldana et al., "Fabrication of Gelatin Methacrylate (GelMA) Scaffolds with Nano- and Micro-Topographical and Morphological Features", Nanomaterials, 9, 120, 12 pages, Aug. 18, 2019.

Aykut et al., "Heparin dose calculated according to lean body weight during on-pump heart surgery", Turkish Journal of Thoracic and Cardiovascular Surgery, vol. 26(4), pp. 528-535, Sep. 16, 2018.

Azizkhan et al., "Mass Cell Heparin Stimulates Migration of Capillary Endothelial Cells In Vitro", J. Exp. Med., vol. 152, pp. 931-944, Oct. 1980.

Bedair et al., "Recent advances to accelerate re-endothelialization for vascular stents", Journal of Tissue Engineering, vol. 8, 14 pages, 2017.

Bhattacharya et al., "Enhanced endothelialization and microvessel formation in polyester grafts seeded with CD34+ bone marrow cells", Blood, vol. 95, No. 2, pp. 581-585, Jan. 15, 2000.

Biran et al., "Heparin coatings for improving blood compatibility of medical devices", Advanced Drug Delivery Reviews, vol. 112, pp. 12-23, 2017.

Björk et al., "Mechanism of the anticoagulant action of heparin", Molecular and Cellular Biochemistry, vol. 48, pp. 161-182 1982.

Bracaglia et al., "Reinforced Pericardium as a Hybrid Material for Cardiovascular Applications", Tissue Engineering, Part A, vol. 20, Nos. 21 & 22, pp. 2807-2816, 2014.

Brown et al., "The Effect of Unfractionated vs. Low Molecular Weight Heparin on Tissue Factor Pathway Inhibitor Levels in Hospital Inpatients", Thromb Haemost, vol. 85, pp. 979-985, 2001.

Cavari et al., "Glycosaminoglycans exposed on the endothelial cell surface Binding of heparin-like molecules derived from serum", FEBS, vol. 323, No. 1.2, pp. 155-158, May 1993.

Chen et al., "Functional Human Vascular Network Generated in Photocrosslinkable Gelatin Methacrylate Hydrogels", Adv. Funct. Mater., vol. 22, pp. 2027-2039, 2012.

Dahan et al., "Dynamic Autologous Reendothelialization of Small-Caliber Arterial Extracellular Matrix: A Preclinical Large Animal Study", Tissue Engineering: Part A, vol. 23, Nos. 1 and 2, pp. 69-79, 2017.

Datta et al., "Peptide-based hydrogels for biomedical applications", Translational Biotechnology A Journey from Laboratory to Clinics, Ch. 8, pp. 203-232, 2021.

(56) References Cited

OTHER PUBLICATIONS

De Graaf et al., "Nitric Oxide Functions as an Inhibitor of Platelet Adhesion Under Flow Conditions", Circulation, vol. 35, No. 6, pp. 2284-2290, published Jun. 1992, downloaded Mar. 21, 2015.

Dela Paz et al., "Arterial versus venous endothelial cells", Cell Tissue Res., vol. 335, pp. 5-16, 2009.

Elineni et al., Regulation of Cell Adhesion Strength by Peripheral Focal Adhesion Distribution, Biophysical Journal, vol. 101, pp. 2903-2911, Dec. 2011.

Etingin et al., "von Willebrand factor mediates platelet adhesion to virally infected endothelial cells", Proc. Natl. Acad. Sci., vol. 90, pp. 5153-5156, Jun. 1993.

Farndale et al., "The role of collagen in thrombosis and hemostasis", Journal of Thrombosis and Haemostasis, vol. 2, pp. 561-573, 2004.

Filová et al., "Improved adhesion and differentiation of endothelial cells on surface-attached fibrin structures containing extracellular matrix proteins", J. Biomed. Mater. Res. Part A, 15 pages, 2013.

Ghista et al., "Coronary artery bypass grafting hemodynamics and anastomosis design: a biomedical engineering review", BioMedical Engineering Online, vol. 12, 28 pages, 2013.

Giraux er al., "Modulation of human endothelial cell proliferation and migration by fucoidan and heparin", European Journal of Cell Biology, vol. 77, pp. 352-359, Dec. 1998.

Han et al., Bioerodable PLGA-Based Microparticles for Producing Sustained-Release Drug Formulations and Strategies for Improving Drug Loading:, vol. 7, Article 185, 11 pages, Jun. 2016.

Han et al., "Surface heparinization and blood compatibility modification of small intestinal submucosa (SIS) for small-caliber vascular regeneration", Bio-Medical Materials and Engineering, vol. 28, pp. 213-222, 2017.

Harskamp et al., "Saphenous Vein Graft Failure After Coronary Artery Bypass Surgery Pathophysiology, Management, and Future Directions", Annals of Surgery, vol. 257, No. 5, pp. 824-833, May 2013.

He et al., "Sustained release of low molecular weight heparin from PLGA microspheres prepared by a solid-in-oil-in-water emulsion method", Journal of Microencapsulation, vol. 28(8), pp. 763-770, 2011.

Hess et al., "Saphenous Vein Graft Failure After Coronary Artery Bypass Surgery Insights From Prevent IV", Cardiovascular Surgery, Circulation, pp. 1445-1451, Oct. 14, 2014.

Hirsh et al., "Mechanism of Action and Pharmacology of Unfractionated Heparin", Arterioscler Thromb Vasc Biol., pp. 1094-1096 Jul. 2001.

Hoshi et al., "The blood and vascular cell compatibility of heparin-modified ePTFE vascular grafts", BioMaterials, vol. 34, pp. 30-41, 2013.

Ijima et al., "Bio-active coating of decellularized vascular grafts with a temperature-sensitive VEGF-conjugated hydrogel accelerates autologous endothelialization in vivo", doi: 10.1002/term.2321, 32 pages.

Ito et al., "Thrombomodulin in disseminated intravascular coagulation and other critical conditions—a multi-faceted anticoagulant protein with therapeutic potential", Critical Care, vol. 23:280, 11 pages, 2019.

Janmaleki et al., "Role of temperature on bio-printability of gelatin methacryloyl bioink in two-step cross-linking strategy for tissue engineering applications", Biomedical Materials, vol. 16, 29 pages, 2021.

Jiang et al., "Mechanocompatible Polymer-Extracellular-Matrix Composites for Vascular Tissue Engineering", Adv. Healthcare Mater., 12 pages, 2016.

Kaplan et al., "Low-thrombogenic fibrin-heparin coating promotes in vitro endothelialization", Journal of Biomedical Materials Research: Part A, 29 pages.

Kasper et al., "Synthesis of poly(propylene fumarate)", Natural Protocols, vol. 4, No. 4, pp. 518-525 2009.

Kato et al., "Direct Determination of Cross-Link Density and Its Correlation with the Elastic Modulus of a Gel with Slidable Cross-Links", ACS Macro Letters, vol. 8, pp. 700-704, May 24, 2019.

Keskin-Erdogan et al., "Utilization of GelMA with phosphate glass fibers for glial cell alignment", J. Biomed. Mater. Res., vol. 109, pp. 2212-2224, 2021.

Khan et al., "Effect of degree of cross-linking on swelling and on drug release of low viscous chitosan/poly (vinyl alcohol) hydrogels", Polym. Bull., 26 pages, 2014.

Khorana et al., "Heparin Inhibition of Endothelial Cell Proliferation and Organization Is Dependent on Molecular Weight", Arterioscler Thromb Vasc Biol., pp. 2110-2115 Oct. 2003.

Kimicata et al., "Assessment of decellularized pericardial extracellular matrix and poly(propylene fumarate) biohybrid for small-diameter vascular graft applications", Acta Biomaterialia, vol. 110, pp. 68-81, 2020.

Kimicata et al., "Extracellular Matrix for Small-Diameter Vascular Grafts", Tissue Engineering, vol. 26, Nos. 23 and 24, pp. 1388-1401, 2020.

Kirkton et al., "Bioengineered human acellular vessels recellularize and evolve into living blood vessels after human implantation", Science Translational Medicine, 11 pages, Mar. 27, 2019.

Klein et al., "A Calorimetric Assay for Chemical Heparin in Plasma", Analytical Biochemistry, vol. 124, pp. 59-64, 1982.

Komiya et al., "Effects of Lignin Derivatives on Cross-Link Density and Dielectric Properties in the Epoxy-Based Insulating Materials for Printed Circuit Boards", IEEE Transactions on Components, Packaging and Manufacturing technology, vol. 3, No. 6, pp. 1057-1062, Jun. 2013.

Koobatian et al., "Successful endothelialization and remodeling of a cell-free small-diameter arterial graft in a large animal model:", Biomaterials, vol. 76, pp. 344-358, 2016.

Lamm et al., "Autologous Endothelialized Vein Allograft A Solution in the Search for Small-Caliber Grafts in Coronary Artery Bypass Graft Operations", Circulation, vol. 104, 7 pages, 2001.

Lawson et al., "Bioengineered human acellular vessels for dialysis access in patients with end-stage renal disease: WO phase 2 single-arm trials", Lancet, vol. 387, pp. 2026-2034, May 14, 2016.

Li et al., "The effect of coimmobilizing heparin and fibronectin on titanium on hemocompatibility and endothelialization", Biomaterials, vol. 32, pp. 4691-4703, 2011.

Li et al., "Designing hydrogels for controlled drug delivery", Nature Reviews, 17 pages, Oct. 18, 2016.

Li et al., "Controlled release of heparin from polypyrrole-poly(vinyl alcohol) assembly by electrical stimulation", www.interscience.wiley.com. 11 pages, published online Mar. 9, 2005.

\* cited by examiner

502

500

200

504

600

502

500

504

606
604
608

602

600

3D PRINTED UV CROSSLINKING MASKS

CROSS-REFERENCE TO RELATED APPLICATION(S)

This application claims priority under 35 U.S.C. § 119 to provisional patent application U.S. Ser. No. 63/261,012, filed Sep. 8, 2021 and titled "System and Methods for Controlled Delivery of Bioactive Materials." The provisional patent application is herein incorporated by reference in its entirety, including without limitation, the specification, claims, and abstract, as well as any figures, tables, appendices, or drawings thereof.

STATEMENT REGARDING FEDERALLY SPONSORED RESEARCH OR DEVELOPMENT

This invention was made with government support under P41 EB023833 awarded by the National Institutes of Health. The government has certain rights in the invention.

TECHNICAL FIELD

The presently disclosed subject matter relates generally to the controlled release and delivery of bioactive materials.

BACKGROUND

The background description provided herein gives context for the present disclosure. Work of the presently named inventors, as well as aspects of the description that may not otherwise qualify as prior art at the time of filing, are neither expressly nor impliedly admitted as prior art.

A major obstacle in the implementation and development of small diameter vascular grafts is the prevention of thrombosis in order to maintain lumen patency. However, despite the range of existing techniques to create antithrombotic grafts, there are no current approaches that address the physiological differences in vascular grafts, namely the disruption of flow at the distal anastomosis and subsequent incidence of thrombosis.

One method to circumvent thrombus formation in tissue engineered vascular grafts is the formation of a pre-implantation endothelial cell lining due to its anti-thrombotic characteristics. The use of a pre-seeded confluent endothelium has been successful in preventing occlusion and most closely mimics native vessels. However, as was previously described by the present inventors, this method limits the off-the-shelf availability of a graft and adds a layer of complexity, which ultimately restricts wide-spread clinical use. See Kimicata et al. "Extracellular Matrix for Small-Diameter Vascular Grafts", *Tissue Eng. Part A* 26, 1388-1401 (2020), which is herein incorporated by reference in its entirety.

Another common approach to inhibit coagulation in vascular grafts is surface treatment for drug delivery. Surface treatments can be eluting or non-eluting and work by way of discouraging platelet adhesion, encouraging endothelial cell attachment, or both. However, eluting treatments typically provide only a short-term burst release and much of the bioactive molecule is washed away, while non-eluting approaches provide localized delivery, but treatment techniques can alter graft properties. Encapsulation in microparticles and incorporation in electrospun fibers have been successful for extending drug release. However, the solvents used in these methods can be harsh and impair loading efficiency, release kinetics, and bioactivity. Alternatively, gelatin methacrylate (gelMA) has been employed to achieve long-term sustained drug release without solvents and its properties can be influenced through UV crosslinking without any impairment to cell viability.

One drug commonly incorporated in vascular grafts to impede thrombosis is heparin. Heparin is an anticoagulant that activates antithrombin III (ATIII), which consequently impedes the activation of multiple factors in the coagulation cascade to inhibit blood platelet aggregation. Heparin has been previously shown to increase the rate of endothelialization through the enhancement of EC adhesion, proliferation, and migration; while in other studies, heparin has been shown to inhibit the proliferation of endothelial cells (ECs) and interfere with normal cell functions. Although the effect of heparin on platelet adhesion is well-established, these opposing results on the relationship between ECs and heparin warrant further investigation to engineer better vascular grafts.

The present inventors previously developed and characterized a vascular graft including decellularized bovine pericardium (dECM) and poly(propylene fumarate) (PPF). See Kimicata et al., "Assessment of decellularized pericardial extracellular matrix and poly(propylene fumarate) biohybrid for small-diameter vascular graft applications", Acta Biomater. 110, 68-81 (2020), which is herein incorporated by reference in its entirety.

This biohybrid (dECM+PPF) graft demonstrated favorable mechanical properties that mimic those of native vessels, with ample strengths to support physiological conditions. Further, in vivo results showed endothelialization of the graft lumen, as well as smooth muscle cell infiltration. However, small diameter vascular grafts are extremely vulnerable to failure by thrombosis over the first month. This reality inspired study to develop a technique for temporally and spatially controllable heparin release that avoids negative effects of heparin on endothelial cells while modulating graft response.

Thus, there exists a need in the art for an apparatus which utilizes UV light exposure as a means of crosslinking can be used to tailor degree of crosslinking, swelling, mechanical properties, and drug delivery.

SUMMARY

The present disclosure presents an interlayer system for controlled delivery of bioactive materials, such as drugs, using masks and selective crosslinking. For example, the present system can be used for the controlled and sustained delivery of heparin loaded in gelMA. Masks can modulate heparin release by way of varying UV exposure in the gelMA. The effects of heparin on endothelial cell behavior and the effect of various heparin release profiles on endothelial cells are also explored in the present disclosure.

More particularly, an innovative interlayer drug delivery system within the dECM+PPF biohybrid vascular graft temporally and spatially modulates the release of heparin through an intermediate gelMA layer. By incorporating 3D printed masks of varying designs, one can spatially control the degree of gelMA crosslinking and consequently facilitate extended heparin release profiles through the biohybrid. The spatial control and localized heparin delivery elicits a unique cell response for small diameter vascular graft applications. The heparin-loaded gelMA layer that sits between the dECM and PPF slowly doses the pericardium with heparin, which diffuses through the dECM to provide sustained release at the surface of the graft. The new system modifies drug delivery to elicit different endothelial cell responses while promoting an antithrombotic environment. The spatial control of heparin release can also be employed to address longitudinal differences along the vascular graft, an area not yet explored in graft design, while temporal profiles can be utilized to balance endothelialization with thrombotic response. Advancements towards off-the-shelf vascular grafts that can be endothelialized are critical to their success and clinical translation.

The following objects, features, advantages, aspects, and/or embodiments, are not exhaustive and do not limit the overall disclosure. No single embodiment need provide each and every object, feature, or advantage. Any of the objects, features, advantages, aspects, and/or embodiments disclosed herein can be integrated with one another, either in full or in part.

It is a primary object, feature, and/or advantage of the present disclosure to improve on or overcome the deficiencies in the art.

It is a further object, feature, and/or advantage of the present disclosure to construct shadow masks that increase the release of heparin, without impacting loading efficiency or drug load. For example, a heparin-loaded gelMA interlayer can provide long-term sustained drug release that can be spatially controlled via 3D printed masks in a biohybrid vascular graft.

In addition to fabricating the gelMA constructs, it is still yet a further object, feature, and/or advantage of the present disclosure to design, fabricate, and optimize the aforementioned shadow masks. For example, computer-aided design (CAD) software can be used to design the masks and to instruct a 3D printer to fabricate the same. Other fabrication methods may also be used to produce suitable masks. After fabrication, supports can be removed and the masks washed with isopropyl alcohol for twenty minutes (20 min). For example, the masks can be crosslinked using a flash box (EnvisionTEC) for a total of two thousand (2000) flashes, in five hundred (500) flash intervals. The masks were 3D printed using resin. The printed mostly crosslinks this material, but after printing the part is cleaned up (e.g., supports and excess resin removed). Crosslinking is then completed using the UV flash box (strobes or flashes of light). Masks can be spray painted black.

It is still yet a further object, feature, and/or advantage of the present disclosure to control the amount of UV light exposure during crosslinking in order to modulate the release of bioactive factors. Patterned masks (see e.g., FIGS. 1A-1B, 2A-2B, 3A-3B, 4A-4B) can be used to pattern release profiles from gelMA. The masks can be 3D printed and so they can be designed and adjusted to fit a range of applications. For example, the masks can be placed over the material (see e.g., FIG. 5A), such as gelatin methacrylate (gelMA), during UV crosslinking (see e.g., FIG. 5B). Masks lead to a reduction in UV light exposure (see e.g., FIG. 6). This reduction in UV light from mask 1 and mask 2 correspond to a decrease in elastic modulus of gelMA (see e.g., FIG. 7), stemming from a decrease in crosslinking. The gelMA can be loaded with heparin, a drug for anticoagulation, and demonstrates that the stiffer the scaffold, the slower the release of heparin (see e.g., FIG. 8).

It is still yet a further object, feature, and/or advantage of the present disclosure to develop a drug delivery technique that will allow temporal and spatial control of unique heparin release profiles (see e.g., FIGS. 9-12).

It is still yet a further object, feature, and/or advantage of the present disclosure to characterize the impact of heparin on endothelial cells (ECs).

It is still yet a further object, feature, and/or advantage of the present disclosure to explore the effects of heparin on HUVECs and found that it is detrimental to their metabolic activity, vWF expression, adhesion, and migration at high concentrations. It is still yet a further object, feature, and/or advantage of the present disclosure to use the dECM+PPF release profiles to study heparin delivery on HUAECs, which demonstrated similar effects, but with a higher sensitivity to heparin than the HUVECs. Furthermore, the unique release profiles from different crosslinking conditions elicited distinct HUAEC response. It is still yet a further object, feature, and/or advantage of the present disclosure to demonstrate the potential of a heparin-loaded gelMA interlayer as an original method to provide long-term sustained drug release that can be spatially controlled via 3D printed masks in a biohybrid vascular graft.

The masks disclosed herein can be used in a wide variety of applications. For example, the effect that heparin has on endothelial cells can be observed by measuring the metabolic activity and von Willebrand Factor (vWF) expression of human umbilical vein endothelial cells (HUVECs) over a large period of time.

The masks can be incorporated into systems or kits which accomplish some or all of the previously stated objectives. For example, aspects concerning the intentional alteration of crosslinking patterns within a construct can be utilized directly by 3D printers themselves.

In certain aspects, the present disclosure includes an interlayer delivery system for bioactive materials, methods of making the interlayer delivery system for bioactive materials, and/or the use of targeted UV light exposure and utilization of the masks to selectively crosslink a scaffold material. The release of bioactive materials may be controlled by adjusting the level of crosslinking. For example, a system for controlled release of heparin may be prepared by applying a UV mask to a gelatin methacrylate material, exposing it to UV light, and then loading the selectively crosslinked material with heparin. In yet another example, the distance between the masks and the crosslinked construct and/or the distance between the light source (e.g. a UV light source) can be adjusted. This adjustment in the distance between components of the system of the crosslinking process can create gradient(s) within the crosslinked construct more and/or less intensely.

According to some aspects of the present disclosure, a method to control localized drug delivery in order to elicit a unique cell response comprises varying light exposure in a photo-crosslinkable material to create a gradient in the crosslinking of the photo-crosslinkable material; loading the photo-crosslinkable material with a drug; and temporally and spatially modulating the release of the drug from the photo-crosslinkable material.

According to some additional aspects of the present disclosure, the photo-crosslinkable material comprises gelatin methacrylate (gelMA). The method can further comprise introducing the gelMA as an interlayer into a bovine pericardium (dECM)+poly(propylene fumarate) (PPF) biohybrid vascular graft. Further, the method can comprise dosing pericardium with heparin, thereby allowing the heparin to be diffused through the dECM to provide sustained release at the surface of the biohybrid vascular graft. Even further, the method can comprise employing the spatial control of heparin release to address longitudinal differences along the biohybrid vascular graft. Even further, the method can comprise utilizing a concentration of heparin low enough to support endothelial adhesion and migration and high enough to prevent platelet adhesion.

According to some additional aspects of the present disclosure, the method can further comprise utilizing a barrier adjacent to the photo-crosslinkable material to substantially prevent diffusion of the drug through the barrier. The barrier can be hydrophobic and can prevent hydrophilic drug(s) from moving therethrough. For example, the barrier can be PPF.

According to some additional aspects of the present disclosure, the method can further comprise slowing the modulated release of the drug with a permeable material. The permeable material can be decellularized bovine pericardium (dECM).

According to some additional aspects of the present disclosure, the method can further comprise modifying drug delivery to elicit different endothelial cell responses and to promote an antithrombotic environment. Endothelialization can be balanced with a thrombotic response.

According to some other aspects of the present disclosure, a mask capable of altering a modulated release profile of a photo-crosslinkable construct comprises a base; a body comprising a substantially opaque material, wherein the body extends from the base, has a height at least two times a height of the base, and includes internal walls that form a pattern, the pattern including at least one aperture; a substantially opaque material applied to and/or forming the body. When light is shown through the body, a gradient is formed in a construct positioned there beneath that depends upon the pattern. The pattern affects a temporal aspect of the release profile associated with the modulated drug release. The pattern can be an amalgamation of at least three distinct sub-patterns.

According to some additional aspects of the present disclosure, the substantially opaque material is applied to a surface of the body.

According to some other aspects of the present disclosure, a drug delivery system for the asymmetric, modulated, and sustained release of a drug comprises a photo-crosslinkable material crosslinked using the mask, the photo-crosslinkable material being loaded with a drug and on a first side of the photo-crosslinkable material, a permeable material that slows a release of the drug. The drug delivery system can further include, on a second side of the photo-crosslinkable material, a barrier adjacent to the photo-crosslinkable material to substantially prevent diffusion of the drug through the barrier.

According to some other aspects of the present disclosure, a method of fabricating a construct comprises synthesizing a gelatin methacrylate (gelMA) construct from type A gelatin and crosslinking the gelMA construct with UV light that has passed through a patterned mask made from a substantially opaque material. GelMA can be crosslinked in a UV box (with constant UV exposure) with a microscope slide and the mask, as appropriate.

According to some other aspects of the present disclosure, the method can further comprise crosslinking the patterned mask with UV exposure in a UV box. Masks can be placed over the microscope slides during crosslinking to attenuate the UV light.

These and/or other objects, features, advantages, aspects, and/or embodiments will become apparent to those skilled in the art after reviewing the following brief and detailed descriptions of the drawings. The present disclosure encompasses (a) combinations of disclosed aspects and/or embodiments and/or (b) reasonable modifications not shown or described.

BRIEF DESCRIPTION OF THE DRAWINGS

Several embodiments in which the present disclosure can be practiced are illustrated and described in detail, wherein like reference characters represent like components throughout the several views. The drawings are presented for exemplary purposes and may not be to scale unless otherwise indicated.

In FIG. 5A, the masks can be placed over microscope slides which are then placed over the material. In FIG. 5B, UV light from a light source is used to crosslink a crosslinkable material, such as gelatin methacrylate (gelMA).

Representative images of vWF and DAPI for HUVECs with various concentrations of heparin in medium at panels c-h 4 h and panels i-n 120 h. Scale bar: 100 µm. Groups with different letters indicate statistical difference. XTT data is presented as mean±propagated error and vWF data is presented as mean±standard deviation.

Figure 11:
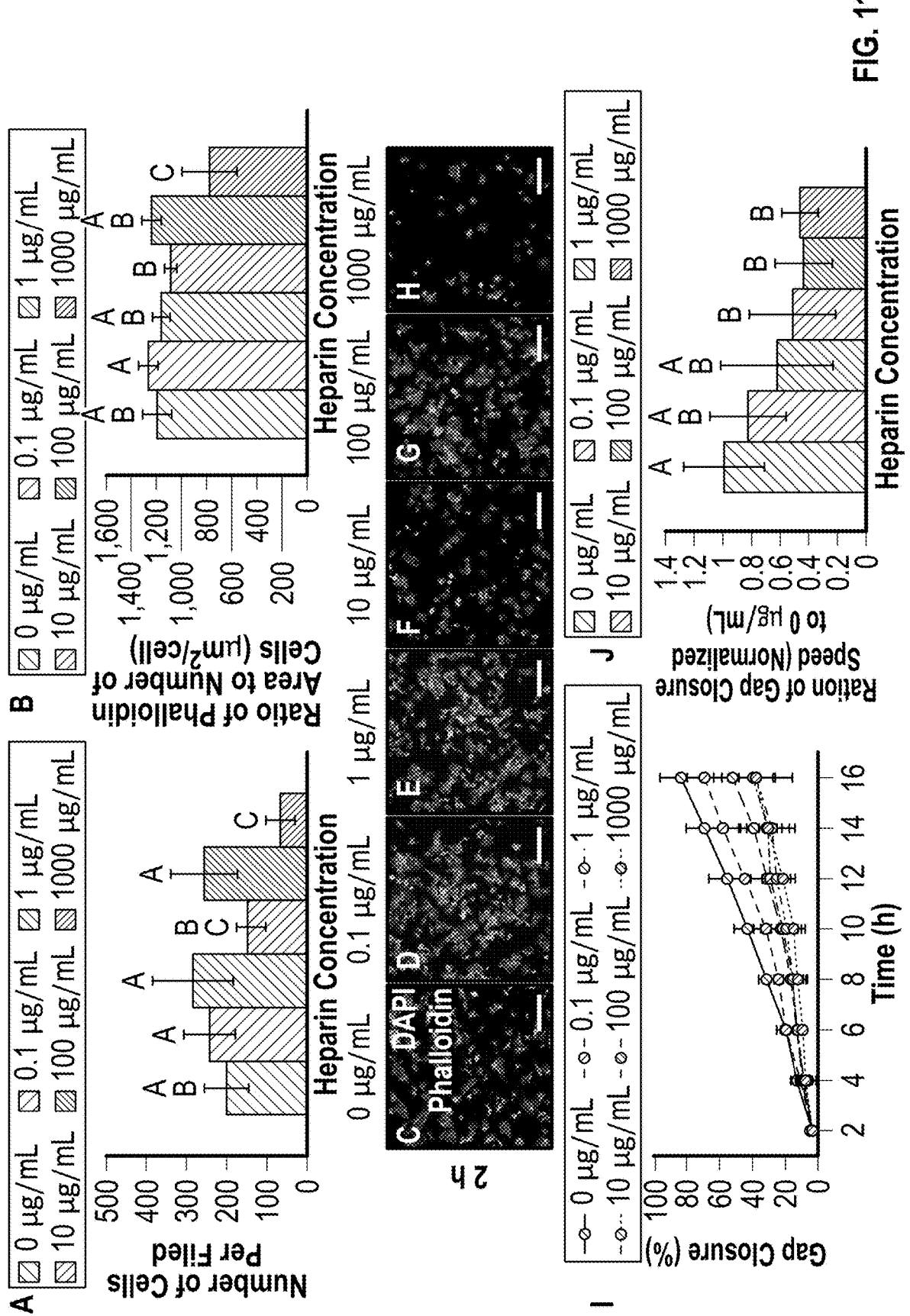

FIG. 11 shows impact of heparin on functionality of HUVECs. Panel a shows a number of HUVECs adhered. Panel b shows a ratio of F-actin area to number of cells 2 h after seeding following 72 h of treatment with various concentrations of heparin in medium. Lower concentrations of heparin support HUVEC attachment and morphology, as indicated by increased number of cells and increased F-actin area per cell, respectively, when compared to higher concentrations of heparin (p<0.05; Tukey multiple comparison; n=9). Panels c-h show representative images of phalloidin and DAPI for HUVECs adhered 2 h after seeding following 72 h of treatment with various concentrations of heparin in medium. Scale bar: 200 µm. Panel i shows a gap closure over 16 h and panel j shows ratio of gap closure speed (normalized to 0 µg/mL) after a straight-line scratch injury. Gap closure and gap closure speed decrease with increasing heparin concentration (p<0.05; Tukey multiple comparison; n=6). Groups with different letters indicate statistical difference. Asterisk (*) denotes statistical difference from 0 µg/mL. Data is presented as mean±standard deviation, except gap closure speed data is presented as mean±propagated error.

Figure 12:
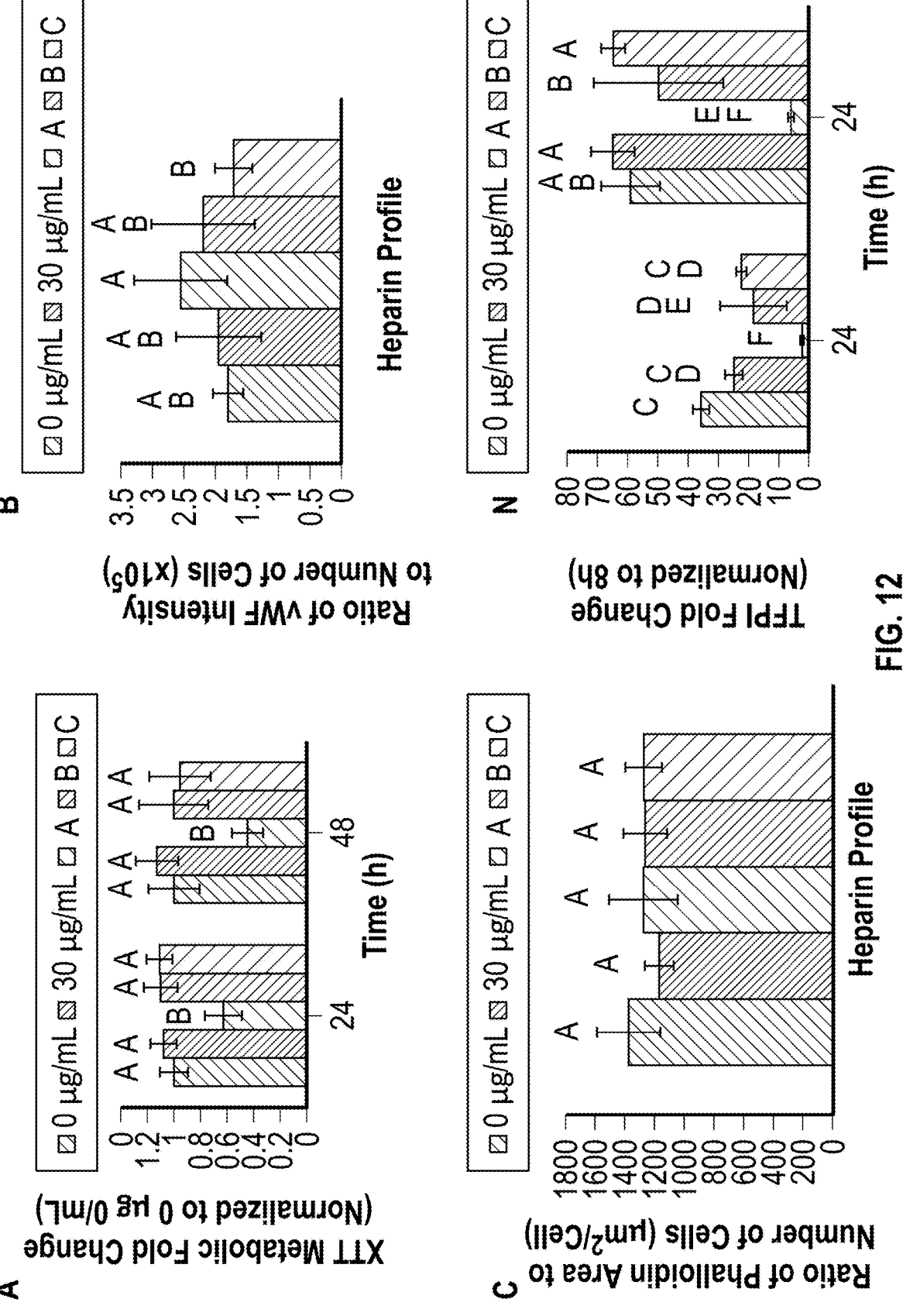
Figure 12:
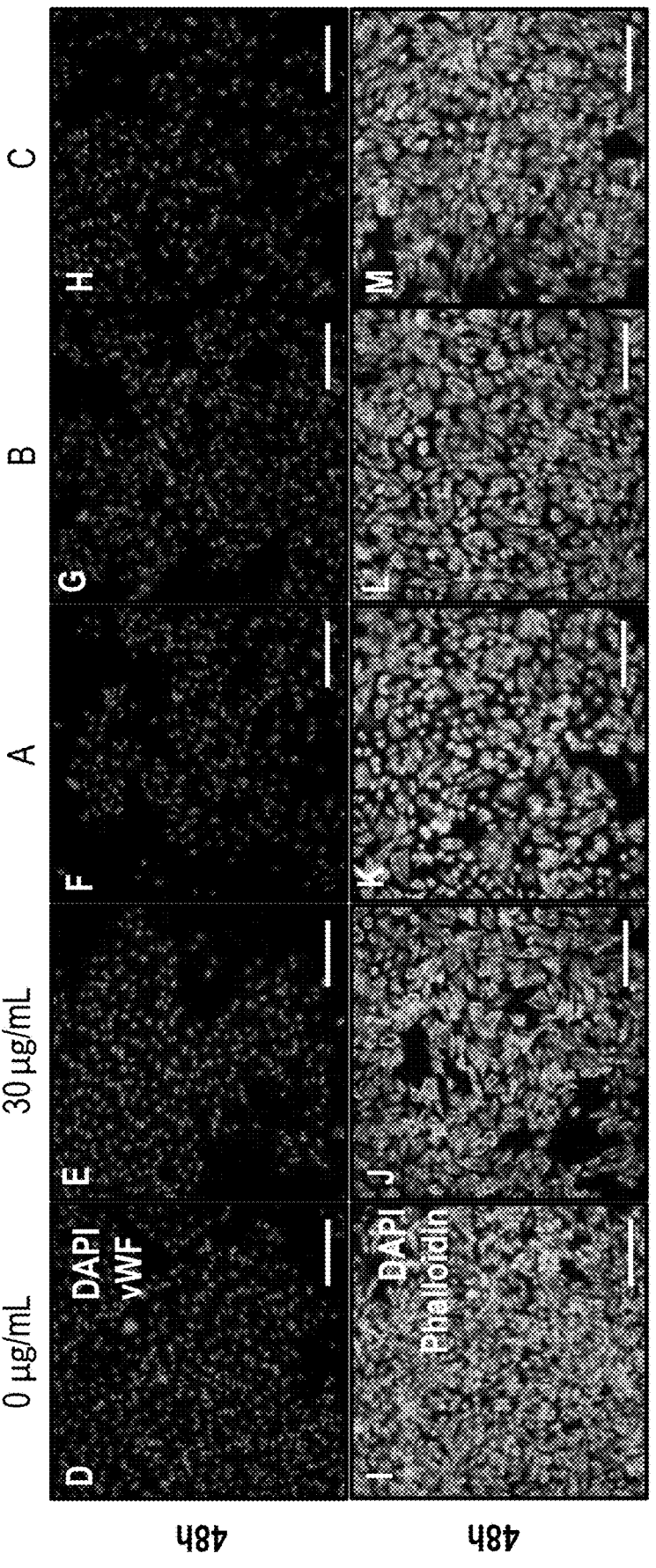

FIG. 12 shows impact of heparin profiles on HUAECs. Panel a shows fold change of the XTT metabolic activity at 48 h (normalized to 0 µg/mL) for HUAECs treated with various heparin release profiles. Heparin profile A reduces the metabolic activity of HUAECs (p<0.05; Tukey multiple comparison; n=9). Panel b shows ratio of vWF intensity to number of cells. Heparin profile A significantly increases the expression of vWF when compared to profile C (p<0.05; Tukey multiple comparison; n=9). Panel c ratio of F-actin area to number of cells at 48 h of treatment is unaffected by differences in heparin profiles (p>0.05; Tukey multiple comparison; n=9). Representative images of vWF and DAPI in panels d-h and phalloidin and DAPI in panels i-m for HUAECs at 48 h with various heparin profiles. Scale bar: 200 µm. Panel n shows TFPI fold change (normalized to 8 h) is negatively impacted by heparin profile A (p<0.05; Tukey multiple comparison; n=9). Groups with different letters indicate statistical difference. All data is presented as mean±standard deviation, except XTT data is presented as mean±propagated error.

An artisan skilled in the art need not view, within isolated figure(s), the near infinite distinct combinations of features described in the following detailed description to facilitate an understanding of the present disclosure.

DETAILED DESCRIPTION

The present disclosure is not to be limited to that described herein. Mechanical, electrical, chemical, procedural, and/or other changes can be made without departing from the spirit and scope of the present disclosure. No features shown or described are essential to permit basic operation of the present disclosure unless otherwise indicated.

Drug delivery and endothelialization are two common approaches to prevent thrombosis in vascular grafts, but current graft technologies fail to address differences along the length of the graft.

Since gelMA is a photocrosslinkable hydrogel, its properties can be readily tuned via UV crosslinking. An original approach to modulate drug release through a gelMA interlayer within the dECM+PPF scaffold by way of UV exposure is shown throughout the figures.

To accomplish this goal, several masks are shown in FIGS. 1A-1B, 2A-2B, 3A-3B, and 4A-4B to reduce the amount of UV light exposure during crosslinking. The reduction in UV light exposure from mask 1 and mask 2 correspond to a decrease in elastic modulus, which affirms the previously established correlation between UV exposure and modulus. Elastic modulus is proportional to density of crosslinks; therefore the use of masks during UV crosslinking results in a decrease in crosslinking density as well. Furthermore, the inverse relationship between elastic modulus and pore size has been well characterized in literature, which suggests that the masks increase pore size and may contribute to differences in drug release, as well.

Figures 1A, 1B, 2A, 2B, 3A, 3B, 4A, 4B:
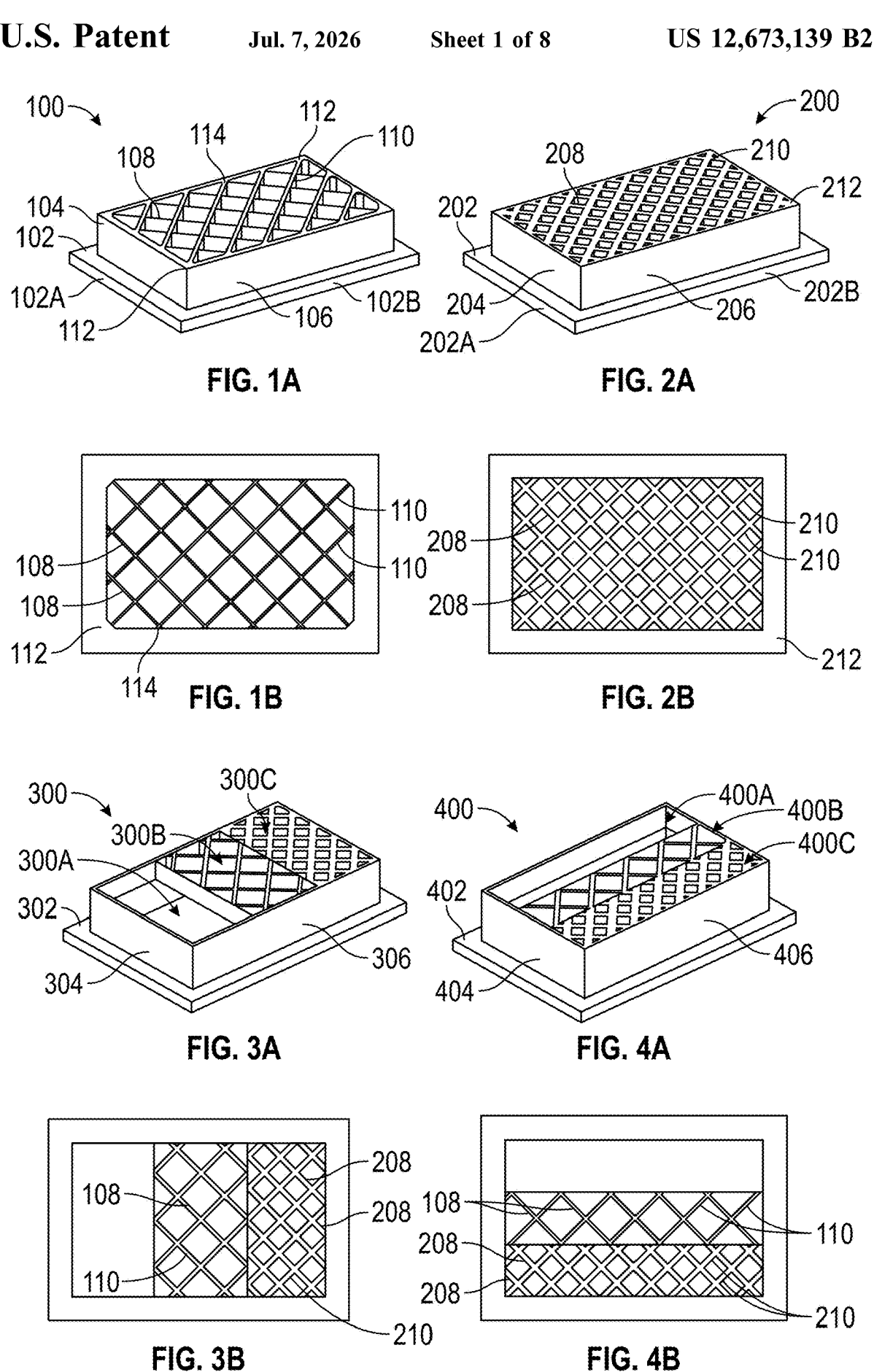
FIG. 1A shows a perspective view of a first exemplary three dimensional (3D) printed mask.
FIG. 1B shows a top plan view of the first exemplary three dimensional (3D) printed mask of FIG. 1A.
FIG. 2A shows a perspective view of a second exemplary three dimensional (3D) printed mask.
FIG. 2B shows a top plan view of the second exemplary three dimensional (3D) printed mask of FIG. 2A.
FIG. 3A shows a perspective view of a third exemplary three dimensional (3D) printed mask.
FIG. 3B shows a top plan view of the third exemplary three dimensional (3D) printed mask of FIG. 3A.
FIG. 4A shows a perspective view of a fourth exemplary three dimensional (3D) printed mask.
FIG. 4B shows a top plan view of the fourth exemplary three dimensional (3D) printed mask of FIG. 4A.

FIGS. 1A-1B show a first example of a mask 100 used for crosslinking a construct. The first mask 100 includes a base 102. While the base 102 can comprise any suitable shape, here the base is shown as a three-dimensional rectangular member 102 that which includes base endwalls 102A and base sidewalls 102B. The body of the mask 100 extends upwardly from the base 102 and includes endwalls 104 and sidewalls 106. The pattern of the first exemplary mask 100 can be described thus. A first set 108 of parallelly oriented "thin" dividing walls perpendicularly intersect a second set 110 of parallelly oriented "thin" dividing walls. In the embodiment shown, the first set 108 of dividing walls is angled at 45° from the sidewalls 106 and the second set 110 of dividing walls is angled at −45°. The pattern is generally uniform from endwall 104 to endwall 104 and from sidewall 106 to sidewall 106, in the area between orthogonal corners 112. Because the dividing walls are thin, the sets 108, 110 of intersecting dividing walls can be further reinforced by additional material at the point of attachment between the walls and the endwalls/sidewalls 104, 106.

FIGS. 2A-2B show a second example of a mask 200 used for crosslinking a construct. The second mask 200 (e.g., includes a base 202, base endwall 202A, base sidewall 202B, body endwall 204, body sidewall 206, a first set 208 of parallelly oriented dividing walls, a second set 210 of parallelly oriented dividing walls, and corners 212) is similar to the first example of a mask 100 used for crosslinking a construct except in that the walls 208, 210 are "thick" and not "thin" and therefore the benefits of any additional reinforcing material is made negligible. The increased density and decreased spacing between each of the dividing walls 208, 210 is also apparent when compared directly to the first example of a mask 100 used for crosslinking a construct.

FIGS. 3A-3B show a third example of a mask 300 used for crosslinking a construct. The third mask 300 includes a pattern with three sub-patterns/sub-sections 300A-C. The third example of a photo-crosslinkable mask 300 can therefore be referred to as a multi-patterned mask.

The first section 300A is positioned adjacent to a first endwall 304 and a second section 300B. As shown, the first section 300A comprises one large opening. The first section 300A therefore allows light to travel unimpeded through the body of the mask 300 and base 302. The second section 300B is positioned adjacent to (between) the first section 300A and the third section 300C. As shown, the second section 300B includes an identical pattern to the pattern shown in the first example of a mask 100 used for crosslinking a construct. The third section 300C is positioned adjacent to the second section 300B and a second endwall 304. As shown, the third section 300C includes an identical pattern to the pattern shown in the second example of a mask 200 used for crosslinking a construct. Each of the first, second, and third sections 300A-300C is located adjacent to both sidewalls 306.

FIGS. 4A-4B show a fourth example of a mask 400 used for crosslinking a construct. The third mask 400 includes a pattern with three sub-patterns/sub-sections 400A-C. The third example of a photo-crosslinkable mask 400 can therefore be referred to as a multi-patterned mask.

The first section 400A is positioned adjacent to a first sidewall 406 and a second section 400B. As shown, the first section 400A comprises one large opening. The first section 400A therefore allows light to travel unimpeded through the body of the mask 400 and base 402. The second section 400B is positioned adjacent to (between) the first section 400A and the third section 400C. As shown, the second section 400B includes an identical pattern to the pattern shown in the first example of a mask 100 used for crosslinking a construct. The third section 400C is positioned adjacent to the second section 400B and a second sidewall 406. As shown, the third section 400C includes an identical pattern to the pattern shown in the second example of a mask 200 used for crosslinking a construct. Each of the first, second, and third sections 400A-C is located adjacent to both endwalls 404.

FIG. 5 shows example schematics regarding the specifics of the crosslinking process. Light 502, such as UV light, from a light source is directed through a mask (e.g., 100, 200, 300, 400, etc.) to a subassembly 600 for crosslinking a construct. The light 502 is attenuated (see shadow 504) through top and bottom microscope slides 606, 608 and onto a construct for delivering drugs. The construct shown is a multi-layered construct that comprises a first layer 602 and a second layer 604. By way of example, the first layer 602 can comprise gelMA and the second layer 604 can comprise dECM.

Figures 5A, 5B, 6:
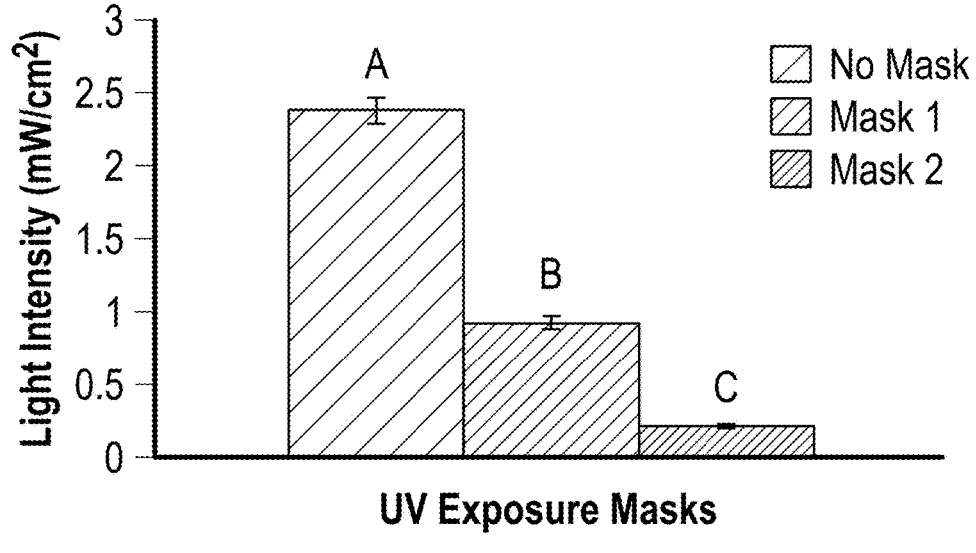
FIGS. 5A-5B show how to implement the masks of FIGS. 1A-1B, 2A-2B, 3A-3B, 4A-4B.
FIG. 6 charts light intensity with no mask, a first mask, and a second mask, according to some aspects of the present disclosure.
Figure 7:
FIG. 7 shows a change in elastic modulus with the first and second masks referenced in FIGS. 1A-1B, 2A-2B, 3A-3B, 4A-4B, according to some aspects of the present disclosure.
Figure 7:
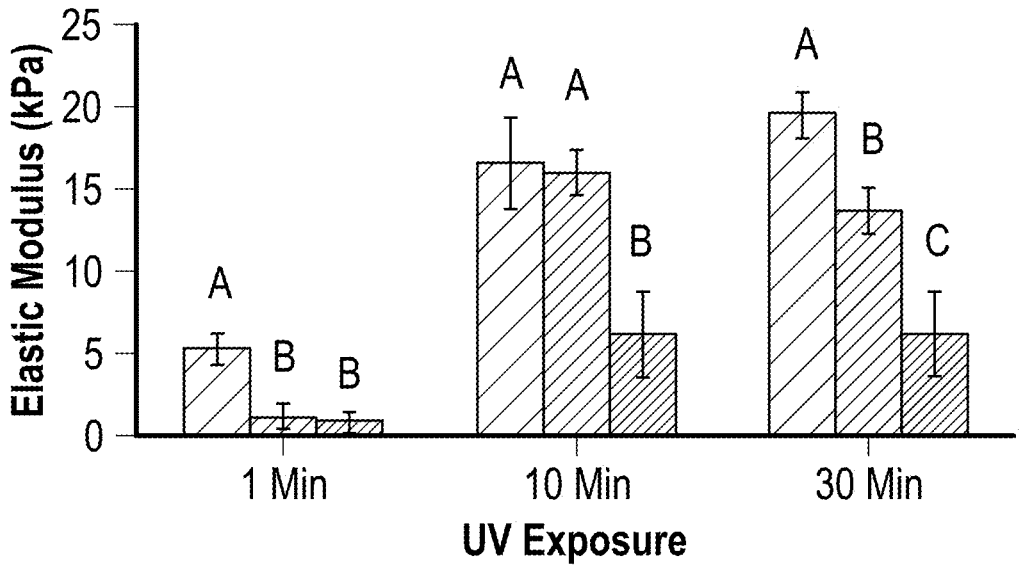

As shown in FIGS. 6-7, the use of no mask and/or different masks will affect light intensity felt by and the resulting elastic modulus of the construct.

Figure 8:
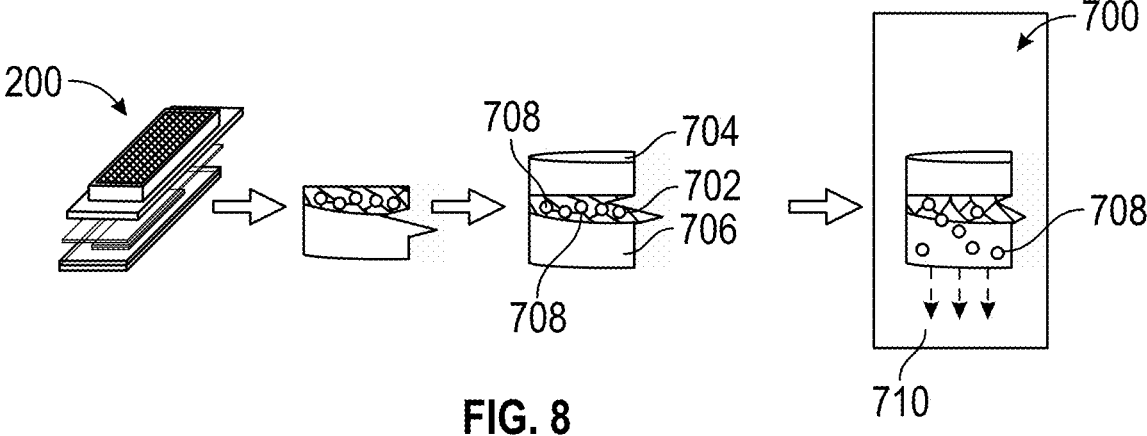
FIG. 8 shows a schematic of a drug delivery system that established the sustained, modulated release of heparin.

As shown in FIG. 8, a drug delivery system 700 comprises (1) an interlayer 702 of the main, photo-crosslinkable material, which in this instance is shown as gelMA; (2) a hydrophobic barrier 704 that does not allow a hydrophilic drug 708 (e.g., heparin) to diffuse into unintended regions of cells and/or tissue, the hydrophobic barrier 704 in this instance being PPF; and (3) a permeable material 706 that allows for a slowed, one-directional release of the drug 708 to the intended target, which in this instance is dECM. The interlayer 702 is loaded with a drug 708, which in this instance is heparin. Use of the construct 700 configured in this manner therefore creates a drug delivery system 700 that sustains the sustained, modulated release 710 of a drug 708, (e.g., heparin).

It should be appreciated that depending on the application and/or drug to be delivered by the drug delivery system, (i) other photo-crosslinkable materials 702 can be used for the interlayer, (ii) other and/or no materials can be used for the hydrophobic barrier 704, and (iii) other and/or no materials can be used for the permeable material 706. The present disclosure is not limited to just the sustained, modulated release 710 of heparin.

Yet, in this specific instance, the purpose of controlling the UV exposure with masks during crosslinking is to create unique heparin release profiles. The loading efficiency in heparin-loaded gelMA is extremely high when compared to other methods of drug encapsulation. There is no clear change in loading efficiency caused by the masks or gelMA concentration, but both of these factors lead to differences in heparin release. The more gradual release in 7%—30 min—No Mask corresponds to higher elastic modulus measured for this group, while the lower elastic moduli measured for 7%—30 min—Mask 1 and 7%—30 min—Mask 2 presented faster heparin release. This trend is supported by previous reports of slower release profiles in hydrogels with more crosslinking, and ultimately decreased pore size. However, due to the extended release of 15% compared to the 7% gelMA, investigations were continued with 15% gelMA in dECM+PPF, despite the significant decrease in drug load.

Next, the heparin-loaded gelMA was incorporated into dECM+PPF to measure the release profile for its application in drug delivery in vascular grafts. When used within the biohybrid material, the masks present the opposite effect on heparin release; the masks present a slower and more sustained release than in the no mask conditions. This change in release profile stems from the subsequent incorporation of PPF. The masks lead to less crosslinking and larger pores across the surface of the sample. Once lyophilized, PPF is better incorporated with gelMA, which reduces the rate of heparin release. Also, with use of masks, heparin is released for at least 14 days, whereas release in the biohybrid without the masks occurs almost entirely within 2 days. This slower, more gradual release is likely to be more beneficial for ECs, while having an extended impact on thrombosis.

Despite the beneficial effects of heparin on the prevention of platelet adhesion, its presence can be disruptive to a variety of cells. It is important to characterize the impact of heparin on endothelial cells to be able to balance supporting endothelialization with its anticoagulant properties. The metabolic activity of HUVECs is sensitive to the presence of heparin and is negatively impacted by dosages between 10 to 1000 µg/mL. The observed decrease in metabolic activity aligns with reported heparin inhibition of $^3$H-thymidine uptake and binding to fibroblast growth factor-2 (FGF-2), which contributes to critical endothelial cell functions like proliferation and migration. The expression of vWF, which is indicative of endothelial dysfunction at elevated levels and plays a role in platelet activation, aggregation, and adhesion, is increased by heparin concentration. This trend, along with the metabolic activity, suggests that HUVECs incur damage from high doses of heparin. These results are aligned with elevated levels of vWF in endothelial cells treated with heparin previously reported.

Adhesion and migration both play a critical role in the endothelialization and homoeostasis of vascular grafts. All concentrations of heparin tested, except 1000 µg/mL, supported the substrate adhesion of HUVECs, as well as the actin area. The phalloidin staining displays decreased actin area, which parallels the collapsed morphology of HUVECs in 1000 µg/mL heparin. Furthermore, heparin concentrations of 10, 100, and 1000 µg/mL significantly reduce the migration of HUVECs. Both of these EC functions are crucial in the success of acellular vascular grafts since endothelialization occurs via attachment of endothelial progenitor cells and migration of ECs across the anastomosis and through the graft wall. The effect of heparin on endothelialization has been debated in literature with investigations yielding results that show an increase in the rate of endothelialization through the enhancement of EC adhesion, migration, and growth, while others conclude that heparin inhibits cell attachment and growth. Our results suggest that lower concentrations of heparin support endothelial adhesion and migration, but higher concentrations are detrimental to endothelialization.

The endothelial response is further characterized to heparin release with HUAECs. Various heparin release profiles were mimicked and measured for the dECM+PPF biohybrid to determine the impact on HUAECs. A quicker release of profile A is detrimental to HUAECs, as revealed by the decrease in XTT metabolic activity, resulting in an increase in vWF expression. Meanwhile, these indicators were unaffected by the slower profiles B and C. When compared to the results for HUVECs, it appears that the cellular activity and vWF expression of HUAECs are more sensitive to the influence of heparin. For the given release profiles of heparin, F-actin area, which corresponds to number of adhered cells above and adhesion strength in literature, is uninhibited. Further, the phalloidin staining shows the characteristic cobblestone morphology of HUAECs in all groups. The slower release profiles correspond to an increase in TFPI, an anticoagulant produced by ECs, and ultimately promote an antithrombotic environment. This phenomenon is consistent with in vitro and clinical results. Furthermore, the elevated levels of TFPI with the slowest heparin profile, profile C, are comparable to the levels of TFPI in 30 μg/mL, a promising result for the clinical relevance of sustained drug release.

EXAMPLES

Mask Fabrication and Use

Mask patterns were designed using SolidWorks and then 3D printed with E-Shell 300 (EnvisionTEC, Detroit, MI) on the EnvisionTEC Perfactory P4. The supports were removed and the masks were washed with isopropyl alcohol for 20 minutes. The masks were crosslinked with a flash box (EnvisionTEC) for a total of 2000 flashes, in 500 flash intervals. Finally, masks were spray painted black. Masks were placed over the microscope slides during crosslinking to attenuate the UV light. The biohybrid release fixture was constructed by the same procedure.

UV Light Measurement

All samples for this study were crosslinked in an AEX-800 UV crosslinker chamber (Ultra-LUM). UV light was measured using the Traceable UV Light Meter (Fisher Scientific). Microscope slides and the appropriate mask were placed on top of the sensor. The UV box was turned on and light was allowed to stabilize for 30 s before the reading was taken. Measurements were taken at 9 different locations inside the UV box (n=9).

GelMA Synthesis

GelMA was synthesized from type A gelatin from porcine skin (gel strength 300, Sigma-Aldrich, St. Louis, MO) as previously described by a co-inventor of the present disclosure.[60] Briefly, gelatin was dissolved in PBS at 50° C. at a concentration of 10% weight/volume. Methacrylic anhydride (0.6 g/1 g gelatin, Sigma-Aldrich) was added dropwise to the solution and left to stir for 1 h. The solution was centrifuged at 2000 g for 2 min. The supernatant was diluted 1:1 in PBS, dialyzed (10 kDa molecular weight cutoff, Thermo Fisher Scientific) and lyophilized.

Compressive Mechanical Testing

Three cylindrical samples were cast from 50 μL of 7 wt % gelMA solution prepared in PBS with 0.1% P-Phenyl-P-(2,4,6-trimethylbenzoyl)phosphinic acid (LAP, Tocris Bioscience, Bristol, United Kingdom) as the photoinitiator for the corresponding UV exposure parameter (n=3). Samples were tested immediately after preparation at room temperature on an Instron 5942 mechanical tester (Instron, Norwood, MA) at a constant compressive displacement rate of 10 mm/min, with a preload of 0.001 N (strain=0). The modulus was calculated from the linear region of the stress-strain curve between 0 and 30% strain.

Biohybrid with Interlayer Preparation

Bovine Pericardium Decellularization Protocol

Native bovine pericardium was decellularized, as previously described. Sheets of native bovine pericardium (Innovative Research, Novi, MI) were cut into 5×5 cm samples. Samples were placed in 20 mL of 1,4-piperazinediethanesulfonic acid (PIPES) solution (8 mM pH 6.8 PIPES (bioWORLD, Dublin, OH), 1 M NaCl (Thermo Fisher Scientific), and 25 mM ethylenediaminetetraacetic acid (EDTA, Sigma-Aldrich, St. Louis, MO) in phosphate buffered saline (PBS)) and agitated on a plate shaker at 100 rpm at room temperature for 15 h. Samples were then washed in PBS three times for 15 min to remove the PIPES solution, placed in 20 mL of sodium dodecyl sulfate (SDS, Sigma-Aldrich) solution (1.8 mM SDS, 1 M NaCl, and 25 mM EDTA in PBS), and agitated on a heated plate shaker at 37° C. at 70 rpm for 7 h. All samples were then rinsed in PBS three times and washed with Medium 200 (Thermo Fisher Scientific, with LSGS), supplemented with 12% fetal bovine serum (FBS, Gibco, Gaithersburg, MD) and 1% Pen Strep (Gibco) for 24 h. Finally, the samples were rinsed thrice with PBS. This procedure resulted in decellularized pericardial extracellular matrix tissue (dECM).

Heparin-Loaded GelMA Application dECM samples were secured on wooden frames and dehydrated with serial ethanol washes (20%, 40%, 60%, 80%, and 100%) for 5 min each with 3 additional 100% ethanol baths for 5 min each and then allowed to air dry. 15 wt % gelMA was prepared in PBS with a heparin concentration of 50 mg/mL and added to the dehydrated dECM. Glass microscope slides were placed under the dECM and on the gelMA mixture with binder clips to secure the materials. GelMA was crosslinked by exposure to UV light for the specified time and mask. The material was then secured and lyophilized.

PPF Synthesis and Application

PPF (number average molecular weight of 1500) was synthesized from propylene glycol (Sigma-Aldrich) and diethyl fumarate (DEF, Sigma-Aldrich) and diluted with DEF in a ratio of 2 parts PPF to 1 part DEF by mass, according to published protocols. See e.g., the following publications naming a co-inventor of the present disclosure: Kasper, et al., "Synthesis of poly(propylene fumarate)", Nat. Protoc. 4, 518-525 (2009); and Bracaglia, et al., "Reinforced Pericardium as a Hybrid Material for Cardiovascular Applications", Tissue Eng. Part A 20, 2807-2816 (2014), both of which are herein incorporated by reference in their entirety. 20 μL of 40% wt/vol bis(2,4,6-trimethylbenzoyl) phenylphosphine oxide (BAPO, Irgacure 819, BASF Corporation, Florham, NJ) in dichloromethane (Thermo Fisher Scientific) was added to the 1.25 g of diluted PPF before UV crosslinking. PPF was added to the gelMA layer. Glass microscope slides were placed under the dECM and on the PPF. Binder clips were placed around the entirety of the microscope slides to secure the materials. PPF was crosslinked by exposure to UV light for 45 min. The biohybrid was washed 8 times with 100% ethanol for 5 min each.

Heparin Loading Analysis

Three cylindrical samples were cast from 50 μL of 7 or 15 wt % gelMA solution prepared in PBS containing heparin at a concentration of 50 mg/mL (with 0.1% LAP) for the corresponding UV exposure parameter. All samples were duplicated without heparin. Samples were lyophilized and weighed before being submerged in 1 mL of 25 U/mL collagenase II (Worthington, Biochemical Corporation, Lakewood, NJ) in PBS and agitated at 37° C. until they were completely digested. The heparin content was quantified using azure A, as previously described. Briefly, a ladder (50 to 0 μg/mL) of heparin was constructed in collagenase. A 0.08 mg/mL azure A (Santa Cruz Biotechnology, Dallas, TX) solution was created in DI water. Samples with heparin were diluted 1:50 in PBS, while samples without heparin were not diluted. 80 μL of each sample/azure A solution (5 μL sample:100 μL of the azure A solution) was loaded into the well plate in triplicate (n=9). The absorbance at 633 nm was measured with a Spark Multimode Microplate Reader. The heparin concentration in each well was quantified by interpolation based on standard curves of known heparin content with the noise from gelMA was removed. The loading efficiency (%) was calculated as follows:

$$loading\ efficiency\ (\%) = \frac{m_{measured} - m_{gelMAsignal}}{m_{theoretical}} * 100\%$$

where $m_{measured}$ is the mass of heparin measured, $m_{gelMA\ signal}$ is the mass from the gelMA noise, and $m_{theoretical}$ is the theoretical mass of heparin in the sample. The drug load (%) was calculated with the equation below $$drug\ load\ (\%) = \frac{m_{measured} - m_{gelMAsignal}}{m_{total}} * 100\%$$

where $m_{total}$ is the total mass of the sample prior to digestion.

Heparin Release

Heparin-Loaded GelMA

Three cylindrical samples were cast from 50 μL of 7 or 15 wt % gelMA solution prepared in PBS containing heparin at a concentration of 50 mg/mL (with 0.1% LAP) for the corresponding UV exposure parameter. Samples were lyophilized and weighed before being submerged in 1 mL of PBS and agitated at 37° C. At each time point, 50 μL of solution was extracted and then immediately replaced with 50 μL of PBS. The heparin content was quantified using azure A. A ladder (80 to 0 μg/mL) of heparin was constructed in PBS. Measurements below 5 μg/mL were assumed to be zero due to the sensitivity of the assay. A 0.08 mg/mL azure A (Santa Cruz Biotechnology, Dallas, TX) solution was created in DI water. Samples were diluted with PBS, as necessary. 80 μL of each sample/azure A solution (5 μL sample:100 μL of the azure A solution) was loaded into the well plate in triplicate (n=9). The absorbance at 633 nm was measured with a Spark Multimode Microplate Reader. The heparin concentration in each well was quantified by interpolation based on standard curves of known heparin content. The released heparin at a given time was calculated as follows:

$$released\ heparin_t = \frac{m_t}{m_\infty}$$

where $m_t$ is the measured mass of heparin at a given time and $m_\infty$ is the measured mass of heparin at the last time point.

Biohybrid with Interlayer dECM+PPF containing the heparin-loaded interlayer constructed from 15% gelMA was fabricated as above. One circular sample (7.5 mm diameter) was collected from three pericardium donors for each group. The samples were fastened at the bottom of a 3D printed fixture (FIGS. 2e) and 1 mL of PBS was added to the fixture. Samples were placed in an incubator at 37° C. for 2 weeks. At each time point, any evaporation loss was accounted for before 50 μL of solution was extracted and then immediately replaced with 50 μL of PBS. The heparin content was quantified using azure A, as described above (n=9).

Cell Metabolic Activity Assay (XTT)

Human umbilical vein endothelial cells (HUVECs) (ThermoFisher Scientific, Waltham, MA) were seeded in 48-well plates at a density of 10,000 cells/well in 1 mL of Medium 200 (with manufacturer's required Low Serum Growth Supplement LSGS, ThermoFisher Scientific). Cells were left overnight to adhere before medium was replaced with 1 mL of treatment medium, which contained 0.1, 1, 10, 100, or 1000 μg/mL heparin in Medium 200 (with LSGS), while the control was medium only. The medium was replaced daily for the duration of this study. The electron coupling and XTT labeling reagents from the Cell Proliferation Kit II (XTT) (Roche, Mannheim, Germany) were mixed according to the manufacturer's protocol and added to the cell medium in a ratio of 1 to 2. Cell medium was removed from the wells and the XTT solution was added. It was incubated for 4 h and 100 μL was extracted in triplicate (n=9). The absorbance was measured with a Spark Multimode Microplate Reader (Tecan, Männedorf, Switzerland). Net absorbance was calculated ($A_{475}$-$A_{650}$) for each sample and XTT fold change was calculated by normalizing the net absorbance to that at 4 h.

Immunostaining

VWF

HUVECs were seeded in 96-well plates at a density of 3,500 cells/well in 235 μL of Medium 200 (with LSGS). Cells were left overnight to adhere before medium was replaced with 200 μL of treatment medium, which contained 0.1, 1, 10, 100, or 1000 μg/mL heparin in Medium 200 (with LSGS), while the control was medium only. The medium was replaced daily for the duration of this study. Cells were fixed with 10% formalin and permeabilized. Wells were treated overnight with anti-von Willebrand factor antibody (1:200, 100 μL, ab9378, Abcam, Cambridge, MA). The secondary antibody used was Alexa Fluor 633 (4 μg/mL, Invitrogen, Carlsbad, CA). Then the cells were stained with DAPI solution (3 μg/mL in PBS) for 10 min. Wells were imaged with an Eclipse Ti2 microscope (Nikon, Tokyo, Japan) under Cy5 excitation (625-650 nm) and emission (670 nm) and DAPI excitation (340-380 nm) and emission (435-485 nm). MATLAB was used to quantify the intensity of the red channel and count the cells in the blue channel for 3 images of each of the 3 wells (n=9) to calculate a ratio of vWF intensity to number of cells.

Actin

HUVECs were treated in culture with treatment medium for 72 h. Treatment medium contained 0.1, 1, 10, 100, or 1000 μg/mL heparin in Medium 200 (with LSGS), while the control was medium only. The medium was replaced daily for the duration of this study. Cells were seeded in 96-well plate at a density of 30,000 cells/well in 200 μL of Medium 200 (with LSGS). Cells were left to adhere for 2 h before the medium was removed. Cells were fixed with 10% formalin and permeabilized. Wells were stained for 1 h with Alexa Fluor 488 Phalloidin (1:100, 100 μL, A12379, Invitrogen). Then the cells were stained with DAPI solution (3 μg/mL in PBS) for 10 min. Wells were imaged with an Eclipse Ti2 microscope under FITC excitation (465-495 nm) and emission (515-555 nm) and DAPI excitation (340-380 nm) and emission (435-485 nm). MATLAB was used to quantify the area of the green channel and count the cells in the blue channel for 3 images of each of the 3 wells (n=9) to calculate a ratio of F-actin area to number of cells.

Scratch Assay

HUVECs were treated in culture with treatment medium for 48 h. Treatment medium contained 0.1, 1, 10, 100, or 1000 µg/mL heparin in Medium 200 (with LSGS), while the control was medium only. The medium was replaced daily for the duration of this study. A 48-well plate was treated for 45 min with 200 µL of 0.1% wt/vol porcine gelatin (Sigma-Aldrich, St. Louis, MO) in DI water at 37° C. Cells were seeded in the well plate at a density of 100,000 cells/well in 800 µL of Medium 200 (with LSGS). Cells were left to adhere for 24 h before the medium was replaced. Scratches were made with a 200 µL pipette tip. Cells were imaged for 1 to 16 h after the scratches were made. ImageJ was used to quantify the gap distance in one image for each well (n=6). Gap closure (%) was reported as $$\text{Gap closure } (\%) = \frac{l_o - l_t}{l_o} * 100$$

where $l_o$ is the original gap length and $l_t$ is the gap length at a given time. The gap closure speed was defined as the slope of gap length curve with respect to time and was normalized to that of the 0 µg/mL group.

HUAECs Heparin Release Study

Human umbilical artery endothelial cells (HUAECs) (Sigma-Aldrich) were seeded in MesoEndo Cell Growth Medium (Sigma-Aldrich) with the appropriate heparin treatment. For XTT and TFPI ELISA measurements, cells were seeded in a 24-well plate at a density of 150,000 cells/well in 1.8 mL of medium, while for immunostaining, cells were seeded in a 96-well plate at a density of 25,000 cells/well in 300 µL of medium. Treatment medium contained the heparin concentrations detailed in Table 1. One control group was medium only, while the other control group contained 30 µg/mL heparin, an estimate of heparin concentration during surgery. The medium was replaced at 8, 24, and 48 h. XTT was conducted as described above at 24 and 48 h. Immunostaining and quantification was completed as described above at 48 h. Tissue factor pathway inhibitor (TFPI) was quantified with DuoSet ELISA kit (R&D Systems, Minneapolis, MN) according to the manufacturer's protocol. The ladder and all samples were run in triplicate (n=9).

TABLE 1

| Heparin profile for HUAECs heparin release study | | | |
|---|---|---|---|
| Heparin | Heparin Concentration (µg/mL) | | |
| Profile | 0 h-8 h | 8 h-24 h | 24 h-48 h | Mask Condition |
| Profile A | 246 | 122 | 118 | 1 min - No Mask |
| Profile B | 259 | 60 | 82 | 30 min - No Mask |
| | | | | 30 min - Mask 1 |
| Profile C | 132 | 78 | 81 | 30 min - Mask 2 |

Statistics

All quantitative assessments of three or more experimental groups were statistically compared using a one-way ANOVA test, followed by a post hoc Tukey's test. All tests assumed equal variance and conducted with 95% confidence intervals (p<0.05).

Results

Development of Shadow Masks

The 3D printed masks: mask 1 (FIGS. 1A-1B) and mask 2 (FIGS. 2A-2B), were designed with varying thickness of an interlaced network to attenuate the intensity of UV light during crosslinking (FIG. 5). The use of no mask, mask 1, and mask 2 each result in significantly different intensities of transmitted light through the mask (p<0.05; Tukey multiple comparison; n=9) (FIG. 6) that consequently lead to a decrease in the elastic modulus of gelMA at 1, 10, and 30 min of UV exposure (p<0.05; Tukey multiple comparison; n=3) (FIG. 7). Specifically, at 1 min both masks lead to a similar decrease in elastic modulus when compared to no mask, while at 10 min, only mask 2 significantly reduces the elastic modulus (p<0.05; Tukey multiple comparison; n=3). At 30 min the elastic modulus significantly decreases with mask 1 and again with mask 2 (p<0.05; Tukey multiple comparison; n=3).

Heparin Release

Figure 9:
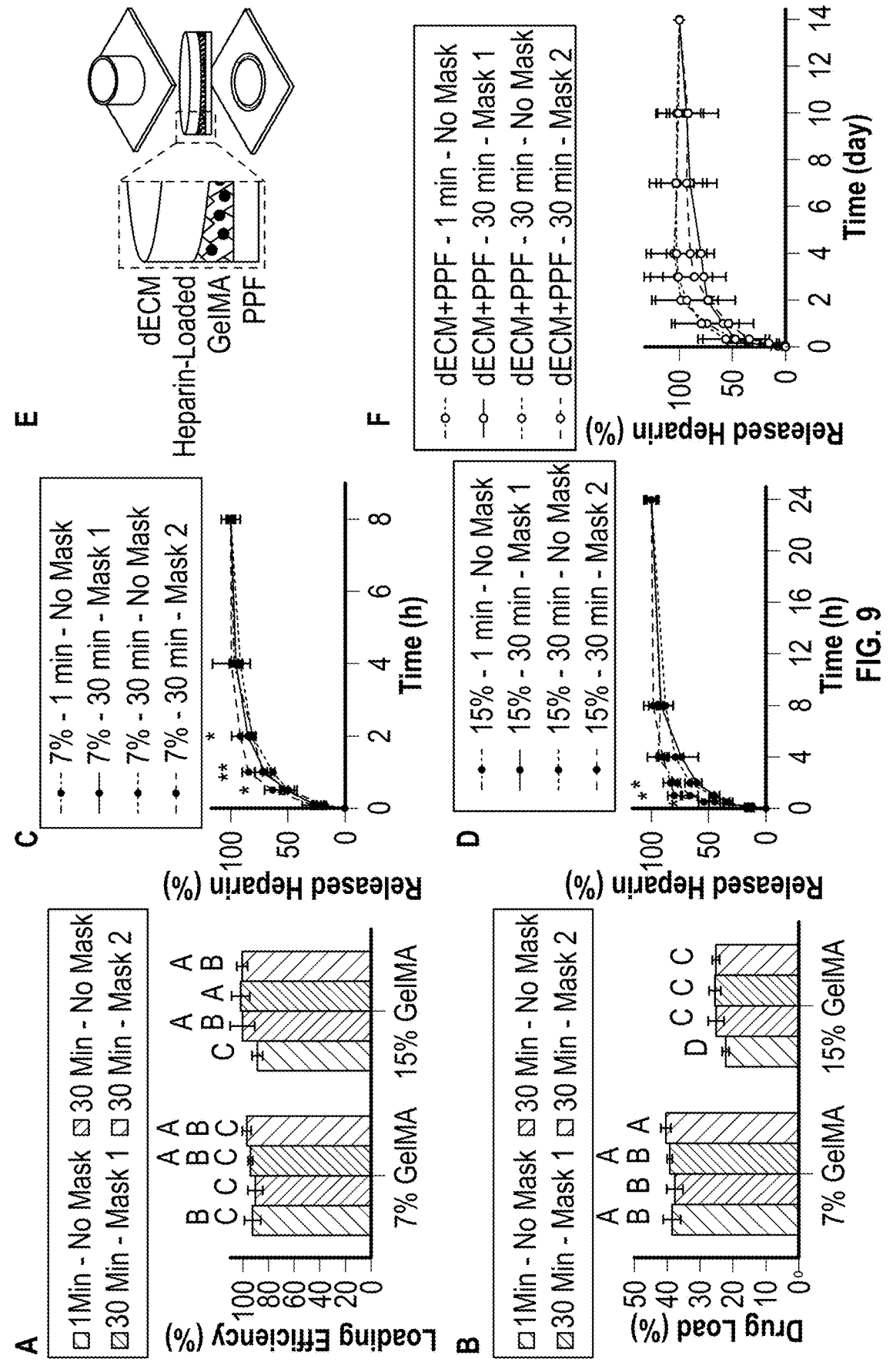
FIG. 9 shows an addition of heparin to gelMA. Panel a shows loading efficiency and panel b shows drug load of heparin in gelMA at a starting concentration of 50 mg heparin/mL of PBS ($p<0.05$; Tukey multiple comparison; n=9). Loading efficiency is at 96%, resulting in a drug load of 39% in 7% gelMA and 24% in 15% gelMA. A burst release of heparin from panel c 7% gelMA occurs within 4 h, which increases to 8 h in panel d 15% gelMA. Mask 2 increases the rate of heparin release in both 7% and 15% gelMA ($p<0.05$; Tukey multiple comparison; n=9). Panel e shows a schematic of the interlayer in the biohybrid material, as well as the biohybrid release fixture. The heparin-loaded 15% gelMA is positioned between decellularized bovine pericardium and poly(propylene fumarate). Panel f shows conversely, mask 1 and mask 2 slow the heparin release from dECM+PPF. One asterisk (*) denotes 30 min—Mask 2 is significantly different than 30 min—No Mask, two asterisks (**) denote 30 min—Mask 2 and 30 min Mask 1 are significantly different than 30 min—No Mask and from each other ($p<0.05$; Tukey multiple comparison; n=9). Loading efficiency and drug load data is presented as mean±propagated error and release data is presented as mean±standard deviation.

Heparin was incorporated into gelMA hydrogels to examine the effects of UV crosslinking masks and gelMA concentration on loading and drug release. A heparin loading efficiency of 96% was observed for gelMA hydrogels without any discernible impact from the UV crosslinking masks (FIG. 9: panel a). A corresponding drug load of 39% for 7% gelMA and 24% for 15% gelMA was calculated for heparin (FIG. 9: panel b). The reduced drug load for the 15% gelMA corresponds to the greater gelMA weight fraction compared to the 7 wt % condition. A burst release of heparin is observed for 7% gelMA with the majority of heparin released by 4 h (FIG. 9: panel c), while a slower release up to 8 h is seen in 15% gelMA (FIG. 9: panel d). Mask 2, which corresponds to the least crosslinked gelMA, results in a significantly increased rate of heparin release in both gelMA concentrations when compared to the 30 min—No Mask condition (p<0.05; Tukey multiple comparison; n=9). Due to its slower and more exaggerated release kinetics, the heparin-loaded 15% gelMA was used to create an interlayer between dECM and PPF (FIG. 9: panel e). Notably, heparin incorporated within the gelMA interlayer of dECM+PPF substantially extended heparin release to days and weeks rather than hours, as seen in gelMA alone. The reduction in UV exposure associated with mask 1 and mask 2 results in a slower heparin release (FIG. 9: panel f), which deviated from similar conditions in gelMA hydrogels. Furthermore, heparin is released from the biohybrid within two to three days in the no mask conditions, whereas the masks provide sustained heparin delivery over 14 days.

Cell Response of HUVECs

Figure 10:
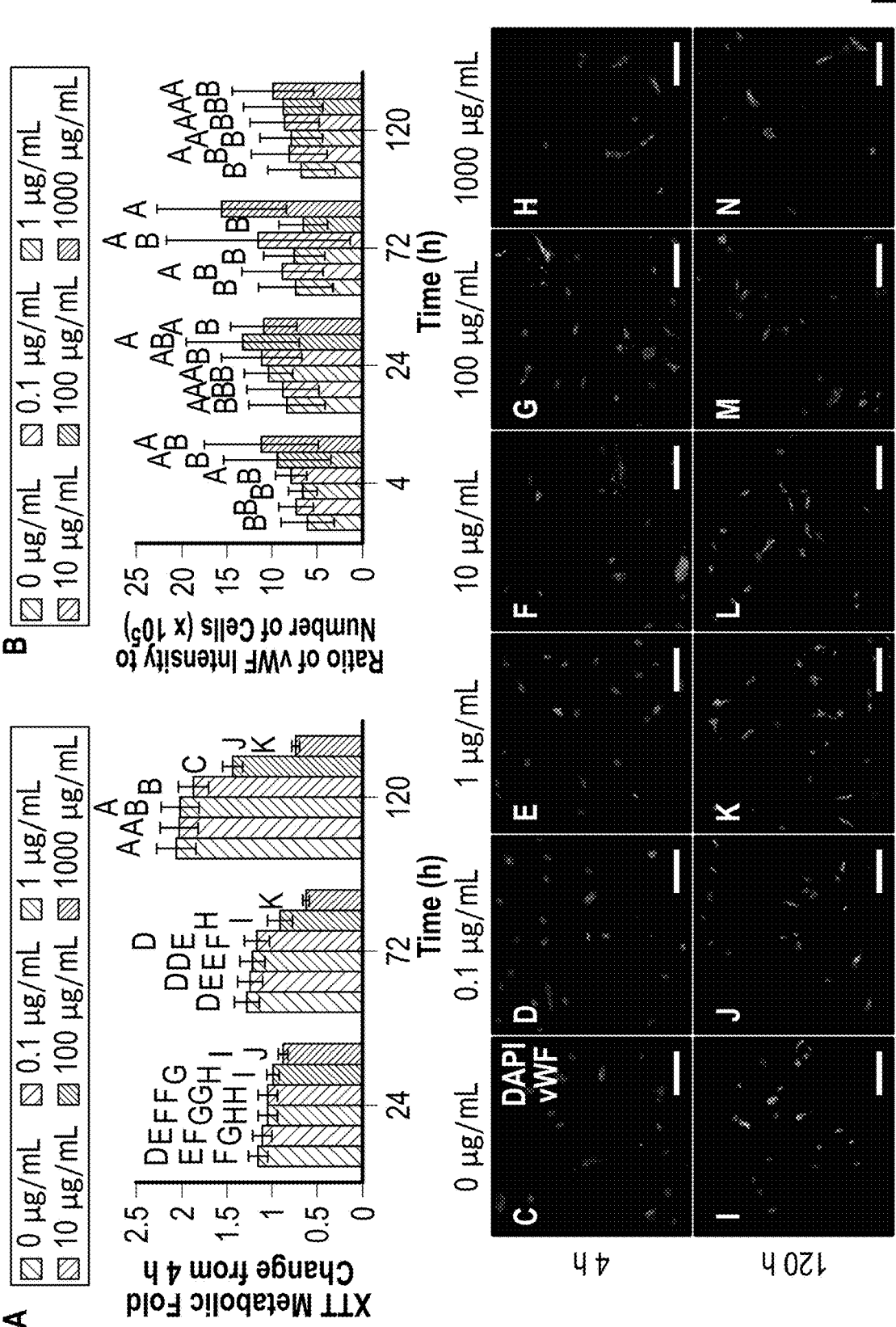
FIG. 10 shows the impact of heparin on HUVECs. Panel a shows fold change of the XTT metabolic activity at 24, 72, and 120 h (normalized to 4 h) for HUVECs treated with various concentrations of heparin in medium. Heparin reduces the metabolic activity of HUVECs at high concentrations ($p<0.05$; Tukey multiple comparison; n=9). Panel b shows a ratio of von Willebrand Factor (vWF) intensity to number of cells, which tends to increase with increasing heparin dose ($p<0.05$; Tukey multiple comparison; n=9).

To understand the effect that heparin has on endothelial cells, the metabolic activity and von Willebrand Factor (vWF) expression of human umbilical vein endothelial cells (HUVECs) was measured over 120 h. Metabolic activity decreases with increasing heparin concentration (FIG. 10: panel a). HUVECs treated with 100 and 1000 µg/mL heparin had significantly decreased metabolic activity at 24, 72, and 120 h when compared to 0 µg/mL heparin (p<0.05; Tukey multiple comparison; n=9). Higher heparin concentrations cause an upward trend in vWF expression in HUVECs (FIG. 10: panel b). FIG. 10: panels c-m show representative images of those used to quantify vWF expression and display the relationship between vWF expression and heparin treatment after 4 and 120 h. Additionally, they show a decrease in cell density at the highest heparin concentrations.

In order to determine the influence of heparin on endothelialization, the impact on the adhesion and migration of HUVECs was first determined. Lower concentrations of heparin, specifically 0.1 and 1 μg/mL, support the number of cells adhered after 2 h (FIG. 11: panel a) and the ratio of F-actin area to number of cells (FIG. 11: panel b). However, these values are significantly lower for 1000 μg/mL when compared to 0 μg/mL (p<0.05; Tukey multiple comparison; n=9). FIG. 11: panel c-h display representative images of those used to quantify number of cells and F-actin area. These images illustrate the reduction in adhered cells, as well as less F-actin in HUVECs with increasing heparin concentration. To investigate the impact of heparin on HUVEC migration, a scratch assay was performed to measure gap closure (FIG. 11: panel i) and the ratio of gap closure speed (FIG. 11: panel j). Heparin significantly decreases the gap closure over 16 h for 1, 10, 100, and 1000 μg/mL and the gap closure speed for 10, 100, and 1000 μg/mL (p<0.05; Tukey multiple comparison; n=6), which indicates that heparin impedes the migration of HUVECs.

Cell Response of HUAECs

To examine the effect of heparin release profiles on endothelialization, the cell response of human umbilical artery endothelial cells (HUAECs) was investigated. The metabolic activity of HUAECs was largely unchanged by heparin profile, except for the faster heparin profile A (p<0.05; Tukey multiple comparison; n=9) (FIG. 12: panel a). Further, HUAECs treated with heparin profile A had a higher vWF intensity than those with the slowest heparin profile, profile C (p<0.05; Tukey multiple comparison; n=9) (FIG. 12: panel b). The phalloidin area ratio was not impacted by the heparin profiles (p>0.05; Tukey multiple comparison; n=9) (FIG. 12: panel c). FIG. 12: panels d-h and FIG. 12: panels i-m exhibit representative images of the effect of heparin profile on vWF expression and phalloidin, respectively, after 48 h. All groups appear to have a similar cobblestone morphology. HUAECs treated with profile A produce significantly less tissue factor pathway inhibitor (TFPI) after 24 and 48 h (p<0.05; Tukey multiple comparison; n=9) (FIG. 12: panel n). After 48 h, profile C and 30 μg/mL demonstrated the highest release of TFPI, which was comparable to 0 μg/mL and significantly more than profile A and profile B (p<0.05; Tukey multiple comparison; n=9).

Closing Matters

The present disclosure investigates an unexplored area in vascular tissue engineering to counter differences along vascular grafts that lead to a higher incidence of thrombosis and graft failure. The present disclosure lays the foundation for a drug delivery tool that allows for temporal and spatial variation in heparin release to balance endothelialization with thrombotic response while maintaining off-the-shelf availability. The present disclosure further develops this system by creating gradients in the crosslinking of gelMA to achieve spatially unique patterns and comparing the in vivo thrombotic response of each.

A drug delivery technique that allows temporal and spatial control of unique heparin release profiles and characterize the impact of heparin on ECs was described. Shadow masks were constructed that increased the release of heparin, without impacting loading efficiency or drug load. The effects of heparin on HUVECs were explored: it was found that heparin on HUVECs is detrimental to their metabolic activity, vWF expression, adhesion, and migration at high concentrations. Lastly, the dECM+PPF release profiles were used to study heparin delivery on HUAECs, which demon-strated similar effects, but with a higher sensitivity to heparin than the HUVECs. Furthermore, the unique release profiles from different crosslinking conditions elicited distinct HUAEC response. The present disclosure demonstrated the potential of a heparin-loaded gelMA interlayer as an original method to provide long-term sustained drug release that can be spatially controlled via 3D printed masks in a biohybrid vascular graft.

From the foregoing, it can be seen that the present disclosure accomplishes at least all of the stated objectives.

LIST OF REFERENCE CHARACTERS

The following table of reference characters and descriptors are not exhaustive, nor limiting, and include reasonable equivalents. If possible, elements identified by a reference character below and/or those elements which are near ubiquitous within the art can replace or supplement any element identified by another reference character.

TABLE 1

| List of Reference Characters | |
| --- | --- |
| 100 | first example of a photo-crosslinkable mask |
| 102 | base |
| 102A | base endwall |
| 102B | base sidewall |
| 104 | body endwall |
| 106 | body sidewall |
| 108 | first set of parallelly oriented "thin" dividing walls |
| 110 | second set of parallelly oriented "thin" dividing walls |
| 112 | corners |
| 114 | reinforced attachments |
| 200 | second example of a photo-crosslinkable mask |
| 202 | base |
| 202A | base endwall |
| 202B | base sidewall |
| 204 | body endwall |
| 206 | body sidewall |
| 208 | first set of parallelly oriented "thick" dividing walls |
| 210 | second set of parallelly oriented "thick" dividing walls |
| 212 | corners |
| 300 | third example of a photo-crosslinkable mask |
| 300A | first section of a multi-patterned mask |
| 300B | second section of a multi-patterned mask |
| 300C | three section of a multi-patterned mask |
| 302 | base |
| 304 | body endwall |
| 306 | body sidewall |
| 400 | fourth example of a photo-crosslinkable mask |
| 400A | first section of a multi-patterned mask |
| 400B | second section of a multi-patterned mask |
| 400C | three section of a multi-patterned mask |
| 402 | base |
| 404 | body endwall |
| 406 | body sidewall |
| 500 | light source |
| 502 | light (e.g., UV light) |
| 504 | shadow (light attenuation) |
| 600 | subassembly for crosslinking a construct |
| 602 | first layer of construct; interlayer |
| 604 | second layer of construct (e.g., permeable material) |
| 606 | top microscope slide |
| 608 | bottom microscope slide |
| 700 | drug delivery system |
| 702 | interlayer (e.g., gelMA) |
| 704 | hydrophobic barrier (e.g., PPF) |
| 706 | permeable material (e.g., dECM) |
| 708 | drug (e.g., heparin) |
| 710 | sustained, modulated drug release |

GLOSSARY

Unless defined otherwise, all technical and scientific terms used above have the same meaning as commonly understood by one skilled in the art to which embodiments of the present disclosure pertain.

The terms "a," "an," and "the" include both singular and plural referents.

The term "or" is synonymous with "and/or" and means any one member or combination of members of a particular list.

As used herein, the term "exemplary" refers to an example, an instance, or an illustration, and does not indicate a most preferred embodiment unless otherwise stated.

The term "about" as used herein refers to slight variations in numerical quantities with respect to any quantifiable variable. Inadvertent error can occur, for example, through use of typical measuring techniques or equipment or from differences in the manufacture, source, or purity of components.

The term "substantially" refers to a great or significant extent. "Substantially" can thus refer to a plurality, majority, and/or a supermajority of the quantifiable variables, given proper context.

The term "generally" encompasses both "about" and "substantially."

The term "configured" describes structure capable of performing a task or adopting a particular configuration. The term "configured" can be used interchangeably with other similar phrases, such as constructed, arranged, adapted, manufactured, and the like.

Terms characterizing sequential order, a position, and/or an orientation are not limiting and are only referenced according to the views presented.

"Endothelialization" refers to the process in which endothelial cells form a monolayer. Endothelialization also refers to the rebuilding/repairing of the inner walls of blood vessels after they have been damaged.

The "invention" is not intended to refer to any single embodiment of the particular invention but encompass all possible embodiments as described in the specification and the claims. The "scope" of the present disclosure is defined by the appended claims, along with the full scope of equivalents to which such claims are entitled. The scope of the disclosure is further qualified as including any possible modification to any of the aspects and/or embodiments disclosed herein which would result in other embodiments, combinations, subcombinations, or the like that would be obvious to those skilled in the art.

What is claimed is:

1. A method to control localized drug delivery to elicit a cell response, the method comprising:

varying light exposure in a photo-crosslinkable material to create a gradient in the crosslinking of the photo-crosslinkable material;

loading the photo-crosslinkable material with a drug; and temporally and spatially modulating the release of the drug from the photo-crosslinkable material;

slowing the modulated release of the drug with a permeable material, wherein the permeable material comprises decellularized bovine pericardium (dECM).

2. The method of claim 1 wherein the photo-crosslinkable material comprises gelatin methacrylate (gelMA).

3. The method of claim 1 further comprising utilizing a barrier adjacent to the photo-crosslinkable material to substantially prevent diffusion of the drug through the barrier.

4. The method of claim 3 wherein the barrier is hydrophobic and prevents hydrophilic drug(s) from moving therethrough.

5. The method of claim 1 wherein the drug comprises more than one drug.

6. The method of claim 1 further comprising modifying drug delivery to elicit different endothelial cell responses and to promote an antithrombotic environment.

7. The method of claim 1 further comprising balancing endothelialization with a thrombotic response.

8. A method to control localized drug delivery to elicit a cell response, the method comprising:

varying light exposure in a photo-crosslinkable material to create a gradient in the crosslinking of the photo-crosslinkable material, wherein the photo-crosslinkable material comprises gelatin methacrylate (gelMA);

loading the photo-crosslinkable material with a drug;

temporally and spatially modulating the release of the drug from the photo-crosslinkable material; and introducing the gelMA as an interlayer into a bovine pericardium (dECM)+poly(propylene fumarate) (PPF) biohybrid vascular graft.

9. The method of claim 8 further comprising slowing the modulated release of the drug with a permeable material.

10. The method of claim 9 wherein the permeable material comprises decellularized bovine pericardium (dECM).

11. A method to control localized drug delivery to elicit a cell response, the method comprising:

varying light exposure in a photo-crosslinkable material to create a gradient in the crosslinking of the photo-crosslinkable material, wherein the photo-crosslinkable material comprises gelatin methacrylate (gelMA);

loading the photo-crosslinkable material with a drug;

temporally and spatially modulating the release of the drug from the photo-crosslinkable material;

introducing the gelMA as an interlayer into a bovine pericardium (dECM)+poly(propylene fumarate) (PPF) biohybrid vascular graft; and dosing pericardium with heparin, thereby allowing the heparin to be diffused through the dECM to provide sustained release at the surface of the biohybrid vascular graft.

12. The method of claim 11 further comprising employing the spatial control of heparin release to address longitudinal differences along the biohybrid vascular graft.

13. The method of claim 11 further comprising utilizing a concentration of heparin low enough to support endothelial adhesion and migration and high enough to prevent platelet adhesion.

* * * * *